US006287856B1

(12) United States Patent
Poet et al.

(10) Patent No.: US 6,287,856 B1
(45) Date of Patent: Sep. 11, 2001

(54) VACCINES AGAINST CIRCOVIRUS INFECTIONS

(75) Inventors: Steven E. Poet, Winterville; Branson W. Ritchie, Athens; Frank D. Niagro, Lawrenceville; Phil D. Lukert, Colbert, all of GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 09/267,177

(22) Filed: Mar. 12, 1999

Related U.S. Application Data

(60) Provisional application No. 60/077,890, filed on Mar. 13, 1998.

(51) Int. Cl.[7] .......................... A01N 63/00; A61K 48/00; C12N 15/00; C07K 1/00; C07H 21/02
(52) U.S. Cl. .................. 435/320.1; 424/93.1; 424/93.21; 424/186.1; 514/44; 530/350; 536/23.1; 536/23.5
(58) Field of Search .................. 424/93.1, 93.21, 424/93.2, 186.1; 435/320.1; 514/44; 536/23.1, 23.5; 530/350

(56) References Cited

PUBLICATIONS

Weiner et al. Scientific American, p. 50–56, Jul. 1999.*
Bebo et al. Journal of Neuroscience Research. 45: 680–689, 1996.*
Barnett et al. Journal of Neuroimmunology. 64: 163–173, 1996.*
Meehan et al. GenEmbl Accession No. PCU49186, Feb. 1997.*
Ledley et al. Pharmaceutical Research. 13: 1595–1614, Nov. 1996.*
Verma et al. Nature. 389: 239–242, Sep. 1997.*
Meehan et al. J General Virology. 78: 221–227, Feb. 1997.*
Raidal et al. Australian Veterinary Journal. 70(12): 437–441, Dec. 1993.*
Vogel et al. Clinical Microbiology Reviews, 406–410, Jul. 1995.*
Ausubel et al. Short Protocols in Molecular Biology 3rd Ed. Wiley and Sons, Inc., 1995.*
Robinson et al. Vaccine. 15(8): 785–787, Jun. 1997.*
Todd et al. Archives of Virology. 117: 129–135, 1991.*
Sato et al. Science. 273: 352–354, Jul. 1996.*
Vogel, F. et al., "Nucleic Acid Vaccines" *Clinical Microbiology Reviews* 8:406–410 (Jul. 1995).
Ritchie, B. et al., Chp. 8 "Circoviridae" In *Avian Viruses Function and Control*; pp.233–252 Wingers Publishing, Inc., Lake Worth Florida (1995).
Meehan, B. et al., "Sequence of Porcine Circovirus DNA:Affinities with Plant Circoviruses" *Journal of General Virology* 78:221–227 (1997).
Ritchie, B. et al., "Characterization of a New Virus from Cockatoos with Psittacine Beak and Feather Disease" *Virology* 171:83–88 (1989).
Mankertz, A. et al., "Mapping and Characterization of the Origin of DNA Replication of Porcine Circovirus" *Journal of Virology* 71:2562–2566 (Mar., 1997).

* cited by examiner

*Primary Examiner*—Deborah J. R. Clark
*Assistant Examiner*—Eleanor Sorbello
(74) *Attorney, Agent, or Firm*—Needle & Rosenberg, P.C.

(57) ABSTRACT

Vaccine compositions which are protective against circovirus infections, including porcine circovirus and psittacine beak and feather disease virus, in animals, comprising a nucleic acid vector comprising a eukaryotic cis-acting transcription/translation regulatory sequence functionally linked to a nucleic acid encoding an animal circovirus polypeptide, wherein the nucleic acid lacks a viral origin of replication are disclosed. Nucleic acid vectors for the transient expression of one or more circovirus polypeptides in a eukaryotic cell comprising a nucleic acid vector comprising a eukaryotic cis-acting transcription/translation regulatory sequence functionally linked to the nucleic acids of the invention are described. Methods of preventing a circovirus-associated disease in an animal comprising administering to the animal a nucleic acid vector comprising a eukaryotic cis-acting transcription/translation regulatory sequence functionally linked to a nucleic acid encoding an animal circovirus polypeptide, wherein the nucleic acid lacks a viral origin of replication are also described. Methods of preventing a circovirus-associated disease in an animal comprising administering to the animal an immunogenic amount of one or more animal circovirus polypeptides are also described. Also disclosed are nucleic acid and polypeptide sequences useful in the vaccine compositions and methods of the invention.

22 Claims, No Drawings

VACCINES AGAINST CIRCOVIRUS INFECTIONS

This application claims priority to U.S. Provisional Patent Application Serial No. 60/077,890 filed Mar. 13, 1998.

FIELD OF THE INVENTION

The field of the invention relates to the diagnosis of and vaccination for circovirus infections in animals.

BACKGROUND OF THE INVENTION

A family of viruses, characterized as round, non-enveloped virions with mean diameters from 17 to 23.5 nm containing circular, single-stranded deoxyribonucleic acid (ssDNA), has been named the Circoviridae, more commonly referred to as circoviruses. Six viruses have been identified as members of the family, according to The Sixth Report of the International Committee for the Taxonomy of Viruses (Lukert, P. D., G. F. de Boer, J. L. Dale, P. Keese, M. S. McNulty, J. W. Randles, and I. Tisher, 1995, The Circoviridae, pp. 166–168. In F. A. Murphy, C. M. Fauquet, D. H. L. Bishop, S. A. Ghabrial, A. W. Jarvis, G. P. Martelli, M. A. Mayo, and M. D. Summers (eds.), Virus Taxonomy, Sixth Report of the International Committee on Taxonomy of Viruses. Arch. Virol. 10 Suppl.).

Animal viruses included in the family are chicken anemia virus (CAV; the type species), beak and feather disease virus (BFDV; also referred to as psittacine beak and feather disease virus), porcine circovirus (PCV), and pigeon circovirus. Three plant pathogens included as unclassified members of the family are the coconut foliar decay virus (CFDV), banana bunchy top virus (BBTV), and subterranean clover stunt virus (SCSV). All members of the Circoviridae have restricted host ranges. The ssDNA genome of the circoviruses represent the smallest viral DNA replicons known.

DNA sequences have previously been published for the plant viruses, CAV (Notebom, M. H. M., G. F. de Boer, D. J. van Roozelaar, C. Karreman, O. Kranenburg, J. G. Vos, S. H. M. Jeurissen, R. C. Hoeben, A. Zantema, G. Koch, H. van Ormont, and A. J. van der Eb, 1991, Characterization of cloned chicken anemia virus DNA that contains all elements for the infectious replication cycle; J. Virol. 65: 3131–3139) and PCV (Meehan, B. M., J. L. Creelan, M. S. McNulty, and D. Todd, 1997, Sequence of porcine circovirus DNA: affinities with plant circoviruses. J. Gen. Virol. 78:221–227; Buhk, H. J. and A. Mankertz, 1996, Sequence analysis of porcine circovirus; GenBank Accession no. Y0992 1). Analysis of the PCV genome indicates that it possesses an ambisense organization. The viral strand encodes a putative replication-associated protein ("Rep"), herein referred to as ORF V1, with all three sequence motifs found in molecules involved in rolling circle DNA replication, and it possesses the P-loop motif.

PCV was originally isolated in porcine kidney cell cultures and was not considered to be a pathogenic virus. In recent years, the presence of PCV has been linked to a progressive, neurological disorder in pigs, sometimes referred to as "shaky pig syndrome". A circovirus has also been implicated in "postweaning multisystemic wasting syndrome" in swine herds in Canada. Thus, there is a need in the art to develop effective vaccines against porcine circoviruses to control these disorders.

Beak and Feather Disease (BFD) is a debilitating disease that, in its chronic phase, is characterized by feather dystrophy and loss, development of beak deformities and eventual death. Peracute and acute disease caused by the same virus are particularly common in neonatal and young birds, where death can occur within a few weeks, or even days, of the first clinical symptoms. The disease has been described in over 40 species of psittacine birds throughout the world, and new species are being added to the list each year. It is thought that the virus originated in Australian birds and spread to other continents through the worldwide movement of birds to support the companion bird industry. No known cures are available, and while vaccination is considered the best opportunity to prevent infections, no safe and economical vaccine has been available prior to this invention (Ritchie, B W 1995 Avian Viruses: Function and Control, Chapter 8, Wingers Publishing, Inc., Lake Worth, Fla.). Thus, there is a pressing need in the art to develop a vaccine to prevent this debilitating disease, particularly in companion birds.

Circovirus infections in pigeons and doves, members of the Columbiformes, have been linked to disease of the gastrointestinal tract, immune system and feathers which can lead to death (Ritchie, B W 1995, Ibid.)

The present invention addresses these needs for a vaccine against circoviruses by providing nucleic acid and subunit vaccines. Specifically, the nucleic acid sequence of the BFD virus is provided as well as a nucleic acid vaccine comprising BFDV or other circoviral nucleic acids.

SUMMARY OF THE INVENTION

The present invention provides vaccine compositions for the protection of animals against circovirus infections. Nucleic acids from beak and feather disease virus, a circovirus that infects avian species, are disclosed. Vaccine compositions comprising naked DNA or mRNA are provided. Subunit vaccines comprising recombinant proteins made from vectors comprising open reading frames from circoviruses are provided. Methods for developing nucleic acid amplification-dependent diagnostic assays, as well as the primers and probes useful in the methods, are also provided.

DETAILED DESCRIPTION OF THE INVENTION

As used herein, the term "polypeptide" refers to a polymer of amino acids and includes full-length proteins and fragments thereof, including peptides.

As used herein, the term "circovirus" refers to a non-enveloped virion containing a circular, single-stranded DNA which is capable of infecting animal cells.

As used herein, "a" or "an" can mean one or more, depending upon the context in which it is used.

The present invention specifically includes the discovery of the nucleic acid sequence of the BFDV genome. The herein disclosed discovery of the nucleic acid sequence of the BFDV genome has allowed a comparison at the genomic level of three animal viruses in the Circoviridae. The comparison reveals that the BFDV and PCV genomes are strikingly similar, while the sequence of a third member, CAV, is more divergent.

For example, the non-coding regions of the PCV and BFDV genomes contain a stem-loop structure, very similar to the so-called structurally conserved element (SCE) in geminiviruses, that is involved in both DNA replication and in control of viral gene expression. In circoviruses, the SCE, which is a stem-loop structure, is flanked by iterated sequences, similar to the iterons described in geminivirus genomes (Arguello-Astorga, G. R., R. G. Guevara-Gonsalez, L. R. Herrera-Estrella, and R. F. Rivera-Bustamante, 1994, Geminivirus replication origins have a group-specific organization of iterative elements: a model for replication; Virology 203:90–100; Mankertz, A., F. Persson, J. Mankertz, G. Blaess, and H.-J. Buhk, 1997. Mapping and characterization of the origin of DNA replication of porcine circovirus. J. Virol. 71:2562–2566). The sequence of the PCV stem-loop structure is: AAGTGCGCT-GCTGTAGTATTACCAGCGCACTT (SEQ ID NO:5). The sequence of the BFDV stem-loop structure is: AGGCGGCGGTTAGTATTACCCGCCGCCT (SEQ ID NO:6).

Another similarity of the BFDV and PCV genome organizations is the arrangement of the coding sequences on the two strands. The Rep protein is encoded by the major viral strand, while the viral capsid or coat protein is encoded on the complementary strand.

Interestingly, consensus TATA sequences are found upstream of the capsid genes (ORF C1), but not in association with the Rep protein genes (ORF V1). Based on the striking similarity between the PCV and BFDV non-coding regions, this invention discloses that a serine codon (TCT) may be used by the psittacine host protein synthesis machinery for initiation of translation.

The PCV and BFDV genomes encode several polypeptide sequences, ranging in approximate size from 8 to 35 kD, as identified by the GeneRunner software program (Hastings Software, Inc., Hastings, N.Y.), Clone Manager (Scientific and Educational Software, State Line Pa.), or the GCG suite of programs. Overall, a comparison of the PCV and BFDV genomes reveals 36% identity at the nucleic acid level. The V1 ORFs from PCV and BFDV encode the replication associated protein (Rep), and an alignment of these two sequences reveals that they have 65% sequence identity at the amino acid level. One feature of the PCV and BFDV Rep protein sequences is the unique sequence of motif 2, in contrast to the reported consensus for this protein (Ilyina, T. V. and E. V. Koonin, 1992, Conserved sequence motifs in the initiator proteins for rolling circle replication encoded by diverse replicons from eubacteria, eucaryotes and archebacteria; Nucl. Acids Res. 20:3279–3285). There is a histidine pair that has been strictly conserved in motif 2 across the archebacteria, eubacteria, geminiviruses, and parvoviruses. However, in the BFDV and PCV sequences, a glutamine has been substituted for the second histidine in this motif. The C1 ORFs encode the capsid protein for the viruses, and these polypeptide sequences contain a high percentage of the basic amino acids arginine and lysine, similar to the coat proteins of luteoviruses.

There is also significant sequence identity between these regions of the capsid protein and the highly conserved sequences of the protamines, which are recognized DNA binding proteins.

Nucleic Acid Vaccines

The present invention provides vaccines comprising circoviral nucleic acids, sometimes referred to as DNA vaccines, although vaccines comprising RNA are also contemplated. Such vaccines are administered to a subject such that they can be expressed in the subject, the polypeptides encoded by the nucleic acid being capable of inducing a protective immune response against a circovirus. General methods for the construction, production and administration of nucleic acid vaccines are known in the art, e.g. Vogel, FR and N Sarver (1995) Clin. Microbiol. Rev. 8:406–410.

The nucleic acid can be any nucleic acid that functionally encodes circovirus polypeptides or fragments thereof. For example, to functionally encode, i.e., allow the nucleic acid to be expressed, the nucleic acid can include, for example, expression control sequences, such as a cis-acting transcription/translation regulatory sequence (including, but not limited to, a promoter, response elements, and an initiator sequence), an enhancer, and information processing sites, such as ribosome binding sites, RNA splice sites, intron elements, polyadenylation sites, and transcriptional terminator sequences, all of which are capable of directing expression in the target animal. Preferred expression control sequences are strong and/or inducible cis-acting transcription/translation regulatory sequences such as those derived from metallothionine genes, actin genes, myosin genes, immunoglobulin genes, cytomegalovirus (CMV), SV40, Rous sarcoma virus, adenovirus, bovine papilloma virus, etc. The nucleic acid is preferably constructed in a vector, such as a plasmid, so that both the viral strand and the complementary strand of the circovirus nucleic acid can be expressed in the target animal. This can be accomplished by including a first expression control sequence to functionally express one strand and a second expression control sequence, which may or may not be the same as the first expression control sequence, to functionally express the other strand. Vectors containing each strand construct are typically mixed together in a 1:1 ratio for administration to the animal, although other ratios may be employed, depending on the particular constructs. A specific embodiment employs constructs using the plasmid "pcDNA3.1$^+$", (InVitrogen Corporation, Carlsbad, Calif.). Alternatively, a single vector can be constructed which would contain two appropriate expression control sequences, as described above, such that the inserted circovirus nucleic acid is transcribed in both directions.

Modifications to the nucleic acids of the invention are also contemplated, since, for example, mutations can thereby be studied for greater protective vaccine effect. Additionally, modifications that can be useful are modifications to the sequences controlling expression of the circovirus sequences, such as modifications to make production of the polypeptides inducible or repressible upon addition to the cells of the appropriate inducer or repressor. Other modifications can be made, as known to the artisan. Such modifications are standard in the art (see, e.g.,. Sambrook et al., *Molecular Cloning. A Laboratory Manual*, 2nd Ed., Cold Spring Harbor Laboratory, Cold Spring Harbor, N.Y., 1989). The nucleic acids can be generated by means standard in the art, such as by recombinant nucleic acid techniques, as exemplified in the examples herein, and by synthetic nucleic acid synthesis or in vitro enzymatic synthesis.

The RNA vaccines of this invention, composed of mRNA encoding circovirus polypeptides, are typically formulated in liposomes (see Martinon et al., 1993, Eur. J. Immunol. 23: 1719–1722), but they can also be administered directly, as described by Yang et al. (1994, J. Cell Biochem. 18A Suppl.:230).

The DNA vaccines are preferably constructed in a plasmid of bacterial origin, and thus the plasmid can be produced in sufficient quantities for administration to the animal to be vaccinated. There are numerous plasmids known to those of ordinary skill in the art useful for the production of DNA vaccine plasmids. In addition to the nucleic acid of the circovirus, the plasmid may contain immunostimulatory sequences ("ISS") in its nucleic acid that stimulate the animals' immune system. Other possible additions to the DNA vaccine construct include nucleic acid sequences encoding cytokines, such as granulocyte macrophage colony stimulating factor (GM-CSF) or interleukin-12 (IL-12). The cytokines can be used in various combinations to fine-tune the response of the animal's immune system, including both antibody and cytotoxic T lymphocyte responses, to bring out the specific level of response needed to protect the animal from the targeted disease.

Alternatively, DNA vaccines can be constructed in a non-replicating retroviral vector, such as the Moloney murine leukemia virus (N2) backbone described by Irwin, et al. (1994, J. Virology 68:5036–5044).

One embodiment of the present invention provides a nucleic acid vector for the transient expression of the double-stranded form of the circovirus genome in a eukaryotic cell comprising a eukaryotic cis-acting transcription/translation regulatory sequence functionally linked to a nucleic acid sequence encoding the entire circovirus genome except for sequences that encode the viral origin of replication, also referred to as the "stem-loop" structure. As discussed above, useful eukaryotic cis-acting transcription/translation regulatory sequences are known in the art.

In a preferred embodiment, the nucleic acid vector comprises selectable marker genes for prokaryotic and eukaryotic expression, cis-acting transcription/translation regulatory sequences derived from the human cytomegalovirus, and cis-acting transcriptional termination seqeuences from the bovine growth hormone gene. In a specific embodiment, provided herein is a nucleic acid vector for the transient expression of a porcine circovirus in a eukaryotic cell comprising a cis-acting transcription/translation regulatory sequence derived from the human cytomegalovirus immediate/early gene enhancer/promoter functionally linked to a nucleic acid of the sequence set forth in either SEQ ID NO:1 or SEQ ID NO:2. In another embodiment, provided herein is a nucleic acid vector for the transient expression of a psittacine beak and feather disease virus in a eukaryotic cell comprising a cis-acting transcription/translation regulatory sequence derived from the human cytomegalovirus immediate/early gene enhancer/promoter functionally linked to a nucleic acid of the sequence set forth in SEQ ID NO:3 or SEQ ID NO:4.

Another embodiment of this invention is a nucleic acid vector for the transient expression of one or more circovirus polypeptides in a eukaryotic cell comprising a eukaryotic cis-acting transcription/translation regulatory sequence functionally linked to a nucleic acid or nucleic acids containing one or more polypeptide-encoding sequences from the circovirus genome. As used herein, a polypeptide is an amino acid sequence encoded by a circovirus open reading frame. Such open reading frames can be identified by any of several computer software programs known in the art, e.g. GeneRunner software program (Hastings Software, Inc., Hastings, N.Y.), Clone Manager (Scientific and Educational Software, State Line Pa.), or the GCG suite of programs. An analysis of SEQ ID NOS: 38, 39, 40 and 41 using such a computer software program demonstrates the existence of open reading frames on both the viral (SEQ ID NOS:38 and 39) and complementary strands (SEQ ID NOS:40 and 41) of the genomes in each of the three possible reading frames. While many organisms use a methionine codon as the initiation codon for an open reading frame, other initiation codons are known and thus a polypeptide of this invention may begin with an amino acid other than methionine.

In a preferred embodiment, the eukaryotic cis-acting transcription/translation regulatory sequence is from cytomegalovirus and the nucleic acid is selected from the group consisting of SEQ ID NO:7, SEQ ID NO:9, SEQ ID NO:11, SEQ ID NO:13, SEQ ID NO: 16, SEQ ID NO:18, SEQ ID NO:20, SEQ ID NO:22, SEQ ID NO:24, SEQ ID NO:25, SEQ ID NO:27, SEQ ID NO:29, SEQ ID NO:31, and SEQ ID NO:33.

Subunit Polypeptide Vaccines

The present invention also provides for vaccines comprising one or more circoviral polypeptides. A nucleic acid encoding such a polypeptide or polypeptides is constructed in a vector suitable for a prokaryotic or eukaryotic host and capable of expressing one or more circovirus polypeptides. There are numerous *E. coli* expression vectors known to one of ordinary skill in the art useful for the expression of the antigen. Other microbial hosts suitable for use include bacilli, such as *Bacillus subtilus*, and other enterobacteriaceae, such as Salmonella, Serratia, and various Pseudomonas species. In these prokaryotic hosts one can also make expression vectors, which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence, and have ribosome binding site sequences for example, for initiating and completing transcription and translation. If necessary, an amino terminal methionine can be provided by insertion of a Met codon 5' and in-frame with the coding sequence. Also, the carboxy-terminal extension of the sequence can be removed using standard oligonucleotide mutagenesis procedures.

Alternative vectors for the expression of circovirus polypeptides in eukaryotic hosts, e.g. mammalian cells, similar to those developed for the expression of human gamma-interferon, tissue plasminogen activator, clotting Factor VIII, hepatitis B virus surface antigen, protease Nexinl, and eosinophil major basic protein, can be employed. Further, the vector can include cytomegalovirus promoter sequences and a polyadenylation signal available for expression of inserted DNAs in eukaryotic cells.

Nucleic Acids and Compositions

Also provided by the invention are nucleic acids that specifically hybridize to the nucleic acids herein disclosed under sufficient stringency conditions to selectively hybridize to the disclosed nucleic acids. Thus, nucleic acids for use, for example, as vaccines or as primers and probes to detect or amplify the target nucleic acids are contemplated herein. Specific or selective hybridization is that hybridization wherein the nucleic acid binds the target nucleic acid with minimal background, nonspecific hybridization to non-target nucleic acids. Typically, the stringency of hybridization to achieve selective hybridization is about 5° C. to 20° C. below the Tm (the melting temperature at which half of the molecules dissociate from its partner), but it is further defined by the salt concentration and the permitivity of the solution. Hybridization temperatures are typically higher for DNA-RNA and RNA-RNA hybridizations. The washing temperatures can similarly be used to achieve selective 20 stringency, as is known in the art. (Sambrook et al., *Molecular Cloning. A Laboratory Manual*, 2nd Ed., Cold Spring Harbor Laboratory, Cold Spring Harbor, N.Y., 1989; Kunkel et al. *Methods Enzymol.* 1987:154:367, 1987).

Nucleic acids for use as primers and probes can be derived from partial or full sequence of the circovirus. Viral sequences at least ten nucleotides in length, which are unique to the virus, can be identified through hybridization studies with the host's DNA to be useful as probes to identify the presence of the virus in samples taken from the host and the host's environs. Upstream and downstream primers of at least six nucleotides, and preferably 18–20 nucleotides, are chosen so that probe sequences can be amplified in samples in order to detect the presence of the circovirus in the host and/or its environs, following procedures known to one skilled in the art (see Niagro et al. 1990 *Proc. Assn. Avian Vet.* 25–37). Samples, such as blood, saliva, tears, organ tissue, sputum, etc. can be obtained by standard methods.

A complete sequence of a porcine circovirus viral strand is presented herein as SEQ ID NO:38, and its complementary strand is presented herein as SEQ ID NO:40. A complete sequence of a psittacine beak and feather disease viral strand is presented herein as SEQ ID NO:39, and its complementary strand is presented herein as SEQ ID NO:41. It is expected that minor variants of the circoviruses of this invention can be isolated through selective hybridization with the sequences disclosed herein. For example, high salt conditions and/or low temperatures of hybridization can be used. For example, the stringency of hybridization is typically about 5° C. to 20° C. below the $T_m$ (the melting temperature at which half of the molecules dissociate from its partner) for the given chain length. As is known in the art, the nucleotide composition of the hybridizing region factors in determining the melting temperature of the hybrid. For 20 mer probes, for example, the recommended hybridization temperature is typically about 55–58° C.

In a specific embodiment, nucleic acids with approximately 90% or greater homology to the nucleic acids of SEQ ID NO:3 and SEQ ID NO:4 are disclosed. As an example, a comparison of a set of nucleotide sequences from three different isolates of BFDV is provided by comparing SEQ ID NO:35, 36, and 37 (272, 268, and 267 nucleotides in length, respectively). Such a comparison demonstrates variation at 20 nucleotides, or approximately 92.7% homology.

The present invention contemplates cells containing a nucleic acid of the invention. A cell containing a nucleic acid encoding a circovirus genome or fragment thereof, or encoding one or more circovirus polypeptides, typically can replicate the DNA and, further, typically can express the encoded circovirus polypeptides. The cell can be a prokaryotic cell, particularly for the purpose of producing quantities of the nucleic acid, or a eukaryotic cell, particularly a mammalian or avian cell, for producing the polypeptides. The cell is preferably a mammalian or avian cell for the purpose of expressing the encoded protein so that the resultant produced protein has the appropriate protein processing modifications.

In one embodiment, a BFDV DNA vaccine preparation of this invention is administered to avian species in combination with one or more DNA vaccine preparations for viral diseases, such as avian polyomavirus, *Chlamydia psittaci*, or Pacheco's disease virus. In another embodiment, the recombinant protein preparation of this invention is administered in combination with one or more recombinant viral proteins from viruses that infect and cause disease in psittacine birds.

In another embodiment, a PCV DNA vaccine preparation of this invention is administered to pigs in combination with one or more DNA vaccine preparations for viral diseases, such as pseudorabies, transmissible gastro-enteritis (TGE), porcine respiratory and reproductive syndrome (PRRS), still birth mummified fetuses embryonic death and infertility (SMEDI), porcine parvovirus, and swine influenza. In another embodiment, the recombinant PCV protein preparation of this invention is administered in combination with one or more recombinant viral proteins from viruses that infect and cause disease in pigs.

Any vaccine composition of this invention can further comprise a pharmaceutically acceptable carrier. The pharmaceutically acceptable carrier in the vaccine of the instant invention can comprise saline or other suitable carriers (Arnon, R. (Ed.) *Synthetic Vaccines* 1:83–92, CRC Press, Inc., Boca Raton, Fla., 1987). An adjuvant can also be a part of the carrier of the vaccine, in which case it can be selected by standard criteria based on the antigen used, the mode of administration and the subject (Arnon, R. (Ed.), 1987). DNA vaccines can be administered in the absence of a traditional adjuvant. or they may be combined with protein components which are typically mixed with adjuvants which are well-known in the art. The DNA vaccines can be incorporated in liposomes or chocleates to enhance in vivo transfection. Genetic adjuvants, such as ISS and cytokine-encoding nucleic acids, can also be employed.

Methods of Vaccination

The present invention further provides methods of vaccinating a subject to induce an immunological response capable of preventing circovirus-associated disease. A BFDV vaccine can be administered to an animal of the avian species, such as poultry, pigeons, doves, and companion birds. In particular, birds which can be treated by the invention can be any of the various species of birds which are classified as being members of the Psittaciformes, Passeriformes or Columbiformes orders. Examples of Psittaciformes birds include, but are not limited to, Budgerigars (*Melopsittacus undulatus*), caiques (e.g., *Pionites leucogaster leucogaster*), macaws (e.g., *Ara ararauna*), Amazon parrots (e.g., *Amazona ochrocephala auropalliata*, conures (e.g., *Pyrrhara picta, Aratinga wagleri wagleri, Aratinga solstitialis, Aratinga guarouba, Aratinga holochlora rubritorquis or Aratinga acuticaudata acuticaudata*), cockatoos (e.g., *Cacatua moluccensis, Cacatua ducorps, Cacatua sulphura, Cacatua goffini or Cacatua alba*), Splendid Parakeets (*Neophema splendida*), Pionus Parrots (*Pionus maximillani*), African Grey Parrots (*Psittacus erithacus erithacus*, Eclectus Parrots (*Electus roratus*), Cockatiels (*Nymphicus hollandicus*) and parakeets (e.g. *Psittacula krameri krameri*). Examples of *Columbiformes* birds include, but are not limited to, pigeons and doves. Examples of *Passeriformes* birds include, but are not limited to, finches and canaries.

Some embodiments of this invention, i.e. a PCV vaccine, can be administered to pigs to prevent circovirus-associated disease.

In one specific embodiment, the present invention provides a method of preventing a circovirus infection in a subject comprising administering to the subject a vaccine comprising an immunizing amount of a nucleic acid vector for the transient expression of a psittacine beak and feather disease virus in a eukaryotic cell comprising a cis-acting transcription/translation regulatory sequence derived from a cytomegalovirus functionally linked to a nucleic acid of the sequence set forth in SEQ ID NO:3 or SEQ ID NO:4.

In another specific embodiment, the present invention provides a method of preventing a circovirus infection in a subject comprising administering to the subject a vaccine comprising an immunizing amount of a nucleic acid vector for the transient expression of a porcine circovirus in a eukaryotic cell comprising a cis-acting transcription/translation regulatory sequence derived from a cytomegalovirus functionally linked to a nucleic acid of the sequence set forth in SEQ ID NO:1 or SEQ ID NO:2.

In one specific embodiment, the present invention provides a method of preventing a circovirus infection in a subject comprising administering to the subject a vaccine comprising an immunizing amount of a nucleic acid vector for the transient expression of one or more circovirus polypeptides in a eukaryotic cell comprising a eukaryotic cis-acting transcription/translation regulatory sequence functionally linked to a nucleic acid sequence encoding a double-stranded form of a circovirus genome minus its origin of replication. In a specific embodiment, this invention provides a method of preventing a circovirus infection in a pig comprising administering to the pig a vaccine comprising an immunizing amount of a nucleic acid vector for the transient expression of one or more porcine circovirus polypeptides in a eukaryotic cell comprising a eukaryotic cis-acting transcription/translation regulatory sequence functionally linked to a nucleic acid sequence selected from the group consisting of SEQ ID NO:22, SEQ ID NO:24, SEQ ID NO:25, SEQ ID NO:27, SEQ ID NO:29, SEQ ID NO:31, and SEQ ID NO:33.

In another specific embodiment, this invention provides a method of preventing a circovirus infection in an avian species comprising administering to the bird a vaccine comprising an immunizing amount of a nucleic acid vector for the transient expression of one or more psittacine beak and feather disease virus polypeptides in a eukaryotic cell comprising a eukaryotic cis-acting transcription/translation regulatory sequence functionally linked to a nucleic acid sequence selected from the group consisting of SEQ ID NO:7, SEQ ID NO:9, SEQ ID NO:11, SEQ ID NO:13, SEQ ID NO:16, SEQ ID NO:18, and SEQ ID NO:33.

Also provided is a method of preventing a circovirus infection in a subject comprising administering to the subject a vaccine comprising an immunizing amount of a nucleic acid vector for the transient expression of one or more circovirus polypeptides in a eukaryotic cell comprising a eukaryotic cis-acting transcription/translation regulatory sequence functionally linked to a nucleic acid sequence encoding a circovirus polypeptide selected from the group of polypeptides with sequences set forth as SEQ ID NO:8, SEQ ID NO:10, SEQ ID NO:12, SEQ ID NO:14, SEQ ID NO:15, SEQ ID NO:17, SEQ ID NO:19, SEQ ID NO:21, SEQ ID NO:23, SEQ ID NO:26, SEQ ID NO:28, SEQ ID NO:30, SEQ ID NO:32, and SEQ ID NO:34.

In another specific embodiment, the present invention provides a method of preventing a circovirus infection in a subject comprising administering to the subject a vaccine comprising an immunizing amount of one or more circovirus polypeptides selected from the group of polypeptides with sequences set forth as SEQ ID NO:8, SEQ ID NO:10, SEQ ID NO:12, SEQ ID NO:14, SEQ ID NO:15, SEQ ID NO:17, SEQ ID NO:19, SEQ ID NO:21, SEQ ID NO:23, SEQ ID NO:26, SEQ ID NO:28, SEQ ID NO:30, SEQ ID NO:32, and SEQ ID NO:34.

Vaccine compositions can be administered to a subject or an animal model by any of many standard means for administering the particular composition. For example, compositions can be administered orally, sublingually, intraocularly, intravenously, by intramuscular injection, intradermally, by intraperitoneal injection, topically, transdermally, or the like. Compositions can be administered alone or in combinations, e.g., as a complex with cationic liposomes, encapsulated in anionic liposomes, enclosed in chochleates, or they can be encapsulated in microcapsules. Compositions can include various amounts of the selected composition in combination with a pharmaceutically acceptable carrier and, in addition, if desired, may include other medicinal agents, pharmaceutical agents, carriers, adjuvants, diluents, etc. Parental administration, if used, is generally characterized by injection. Injectables can be prepared in conventional forms, either as liquid solutions or suspensions, solid forms suitable for solution or suspension in liquid prior to injection, or as emulsions.

In one embodiment, a vaccine of this invention, whether a protein or a DNA vaccine, is administered on a regular booster schedule, for example, every six months or annually. The vaccine may be advantageously administered to animals orally, such as in pill form, or intranasally in a spray, or intraocularly in a drop. Alternatively, the vaccine may be administered intramuscularly, subcutaneously or intradermally.

The following examples are intended to illustrate, but not limit, the invention. While they are typical of those that might be used, other procedures known to those skilled in the art may be alternatively employed.

Throughout this application, various publications are referenced. The disclosures of these publications in their entireties are hereby incorporated by reference into this application in order to more fully describe the state of the art to which this invention pertains.

EXAMPLES

Example 1
Sequencing of the BFDV Genome

It is not currently possible to propagate the BFDV virus in cell culture. Consequently, virus must be harvested from diseased animals for sequencing. Animals used in this study were humanely euthanized, diseased birds which had been donated to the University of Georgia College of Veterinary Medicine for psittacine disease research. Virus was purified from the skin of diseased birds according to published procedures (Ritchie, B. W., F. D. Niagro, P. D. Lukert, W. L. Steffens, and K. S. Latimer, 1989, Characterization of a new virus from cockatoos with psittacine beak and feather disease, Virology 171:83–88). Virus suspensions were extracted sequentially with equal volumes of Tris-saturated phenol and chloroform-isoamyl alcohol (24: 1), and precipitated with ethanol. Viral DNA was digested with restriction endonuclease Hha-I. The digestion products were separated by electrophoresis. Bands were excised from the gel and the DNA fragments extracted using a crush and soak method. Individual eluted DNA fragments were end labeled and sequenced by the chemical cleavage method (Ambrose, B. J. B and R. C. Pless, 1987, DNA sequencing: Chemical methods, pp 522–538, In S. L. Berger and A. R. Kimmel (ed.), Methods in Immunology, Vol 152, Guide to molecular cloning techniques, Academic Press, New York, N.Y.). The sequence from one Hha-I fragment was used to design a pair of oppositely oriented primers for amplification of the remainder of the viral DNA by inverse PCR.

Primers FN 1 (5'-GCTCTAGATGATCCTCCGGAGATTACG) and FN2 (5'-GCTCTAGAGGGAACCATGCCGTCCAA) were designed with restriction endonuclease Xba-I cleavage sites at their 5' ends, for subsequent cloning of the amplimer into pUC-1 9. The full sequence was determined by a deletional subcloning and by sequencing of PCR products from several virus isolates. Sequence runs were assembled into the consensus sequence using manual methods and the fragment assembly programs in the GCG suite of programs (Devereux. J., P. Haeberli, and 0. Smithies, 1984, A comprehensive set of sequence analysis programs for the VAX, Nucl. Acids Res. 12:387–395).

Example 2
Sequencing of the PCV Genome

A PCV-infected porcine cell line PK-15 (ATCC CCL-3) was obtained from the American Type Culture Collection.

Cells were grown in Earle's minimal essential medium with 10% fetal bovine serum at 37° C. in 5%CO2. DNA from cultured cells and tissues was purified using two rounds of proteinase K digestion and salt precipitation. PCR was performed to amplify viral DNA which might be similar to the BFDV genome. Primers were designed based on amino acid sequence conservation among the reported plant circoviruses and the psittacine beak and feather disease virus sequences. Using primers FN 18 (5'-CCCCTCTTTACTGCAGTA-3') and FN 19 (5'-TGTCGCCGTTGGTGTTTC-3'), designed from the reverse-translation of conserved amino acid sequences, an arbitrary primer thermal cycling profile was used to amplify PCV DNA corresponding to the potentially conserved region of sequence. A 900 base pair fragment was labeled with digoxigenin and used to probe unamplified DNA isolated from PK-15 cells and from the uninfected control ESK-4 cells (American Type Culture Collection, Rockville, Md., USA, CL 184). The probe was also used in an in situ hybridization experiment on PCV infected PK-15 cells and a line of PK-15 cells developed at the National Animal Disease Laboratory, Ames, Iowa, USA, which were identified as PCV negative. The results of that experiment suggested that a small percentage of PK-15 infected (ATCC) cells contained nucleic acid complementary to the 900 base pair probe. This corresponded to the small percentage of cells previously demonstrated to exhibit PCV antigen, using immunocytochemical techniques (Hines, R. K. and P. D. Lukert, 1997, Porcine circovirus as a cause of congenital tremors in newborn pigs, p. 344; In Proceedings of the American Association of Swine Practitioners, Quebec City, Canada). The 900 base pair fragment was sequenced and several oligonucleotides were synthesized for use as PCR primers. Amplified DNA fragments were sequenced by dye terminator cycle sequencing. Complementary sequencing runs from PCR generated PCR fragments were aligned using the ALIGN program. Sequence runs were manually assembled into the complete continuous sequence. PCR primers were chosen with the help of the GENE RUNNER program (Hastings Software, Hastings, N.Y.).

Example 3
Structure of the BFDV genome

Analysis of the BFDV genome sequence revealed that it had an ambisense organization, i.e. both the ssDNA of the virus, as well as the complementary DNA strand that is synthesized in the host, encode polypeptides. Northern blot analyses, using strand-specific oligonucleotides to probe polyadenylated RNA from BFDV infected feather pulp, confirmed the ambisense organization. The viral strand possesses a major open reading frame (ORF), V1, which encodes a putative replicase protein, possessing all rolling circle replication sequence motifs and the P-loop motif. A second major ORF (V2) is encoded in a different reading frame on the viral strand. The BFDV complementary strand encodes a capsid protein, including a highly conserved sequence of 14 amino acids (YVtkLTIYVQFRqF) near the carboxyl terminus of the protein as well as adjacent corresponding myristylation sites.

Example 4
Analysis of the PCV Genome

Further analysis of the inferred complementary strand of PCV has revealed another open reading frame, ORF C1. This ORF is flanked by eukaryotic transcription control and polyadenylation signals. The deduced amino acid sequence of this protein possesses a high percentage of arginine and lysine residues near the amino terminus. The non-coding region separating the beginnings of both oppositely oriented ORFs contains features suggestive of replication and transcription control functions. Two additional major ORFs are present (one on each strand).

Example 5
Vaccination of Birds with a DNA Vaccine

A DNA vaccine comprising a cytomegalovirus cis-acting transcription/translation regulatory sequence (pCDNA 3.1+ from InVitroGen Corporation, Carlsbad, Calif.) functionally linked to a nucleic acid of SEQ ID NO:1 was produced in *E.coli*, and the plasmid was purified using commercially available DNA purification columns. Chickens were injected with 50 µg plasmid intramuscularly. The birds received a booster vaccination of 50 µg two weeks after the initial injection. Birds are boosted annually thereafter.

SEQ LISTINGS:

SEQ NO:1 The porcine circovirus genome sequence of nucleotides 38–1711 (based on the linear map of Meehan, Pcv1.Seq, accession U49186)

SEQ NO. 2: The porcine circovirus genome sequence of nt 13- nt 1739

SEQ NO. 3: The psittacine beak and feather disease virus genome sequence of nt 72–1984

SEQ NO:4: The psittacine beak and feather disease virus genome sequence of nt 21–1984

SEQ ID NO:5: (stem-loop structure from PCV) AAGTGCGCTGCTGTAGTATTACCAGCGCACTT

SEQ ID NO:6 (stem-loop structure from BFDV) AGGCGGCGGTTAGTATTACCCGCCGCCT

SEQ ID NO:7 (VI orf from BFDV)
nucleotides 345–1004 (viral strand numbering)

SEQ ID NO:8 (deduced aa sequence for SEQ ID NO:7)
MLPR . . . PINF

SEQ ID NO:9 (V2 orf from BFDV)
nucleotides 550–1023 (viral strand numbering)

SEQ ID NO:10 (deduced aa sequence for SEQ ID NO:9)
MGGA . . . LGDV

SEQ ID NO:11 (V3 orf from BFDV)
nucleotides 1019–1240 (viral strand numbering)

SEQ ID NO:12 (deduced aa sequence for SEQ ID NO:11)
MFN . . . SLY

SEQ ID NO:13 (C1 orf from BFDV)
nucleotides 20–751 (complementary strand numbering)

SEQ ID NO:14 (deduced aa sequence for SEQ ID NO:13)
SNYA . . . NPST

SEQ ID NO:15 (deduced aa sequence for SEQ ID NO:13, with a Met start codon)
MEMR . . . NPST (translation starts at nucleotide 326)

SEQ ID NO:16 (C2 orf from BFDV)
nucleotides 57–218 (complementary strand numbering)

SEQ ID NO:17 (deduced aa sequence for SEQ ID NO:16)
MPAH . . . VLAT

SEQ ID NO:18 (C3 orf from BFDV)
nucleotides 1428–1898 (complementary strand numbering)

SEQ ID NO:19 (deduced aa sequence for SEQ ID NO:18)
MQAP . . . LTGA

SEQ ID NO:20 (V1 orf from PCV)
nucleotides 47–982 (viral strand numbering)

SEQ ID NO:21 (deduced aa sequence for SEQ ID NO:20)
MPSKK . . . KINY

SEQ ID NO:22 (V2 orf from PCV)
nucleotides 1163 –1447 (viral strand numbering)

SEQ ID NO:23 (deduced aa sequence for SEQ ID NO:22)
  MEPQ . . . VLER
SEQ ID NO:24 (C1 orf from PCV)
  nucleotides 37–735 (complementary strand numbering)
SEQ ID NO:25 (C1 alt-orf from PCV)
  nucleotides 37–723 (complementary strand numbering)
SEQ ID NO:26 (deduced aa sequence for SEQ ID NO:25)
  MTWP . . . ILKD
SEQ ID NO:27 (C2 orf from PCV, in SEQ 1 construct)
  nucleotides 1102–1719 (complementary strand numbering)
SEQ ID NO:28 (deduced aa sequence for SEQ ID NO:27)
  MISIP . . . WHFH
SEQ ID NO:29 (C2 orf from PCV, in SEQ 2 construct)
  nucleotides 1102–1710 (complementary strand numbering)
SEQ ID NO:30 (deduced aa sequence for SEQ ID NO:29)
  MISIP . . . FLAW
SEQ ID NO:31 (C3 orf from PCV)
  nucleotides 1200–1544 (complementary strand numbering)
SEQ ID NO:32 (deduced aa sequence for SEQ ID NO:31)
  MTCT . . . NPWR
SEQ ID NO:33 (alt-C2 orf from BFDV)
  nucleotides 12–218
SEQ ID NO:34 (deduced aa sequence for SEQ ID NO:33)
  GAPL . . . VLAT

What is claimed is:

1. An isolated nucleic acid comprising a nucleic acid having a nucleotide sequence with 90% or greater homology to a sequence selected from the group consisting of: SEQ ID NO:3, SEQ ID NO:4, SEQ ID NO:6, SEQ ID NO:7, SEQ ID NO:9, SEQ ID NO:11, SEQ ID NO:13, SEQ ID NO:16, SEQ ID NO:18, SEQ ID NO:33, SEQ ID NO:35, SEQ ID NO:36, SEQ ID NO:37, SEQ ID NO:39, and SEQ ID NO:41.

2. The nucleic acid sequence of claim 1, wherein the nucleic acid sequence comprises SEQ ID NO:3.

3. The nucleic acid sequence of claim 1, wherein the nucleic acid sequence comprises SEQ ID NO:4.

4. The nucleic acid sequence of claim 1, wherein the nucleic acid sequence comprises SEQ ID NO:7.

5. The nucleic acid sequence of claim 1, wherein the nucleic acid sequence comprises SEQ ID NO:9.

6. The nucleic acid sequence of claim 1, wherein the nucleic acid sequence comprises SEQ ID NO:11.

7. The nucleic acid sequence of claim 1, wherein the nucleic acid sequence comprises SEQ ID NO:13.

8. The nucleic acid sequence of claim 1, wherein the nucleic acid sequence comprises SEQ ID NO:16.

9. The nucleic acid sequence of claim 1, wherein the nucleic acid sequence comprises SEQ ID NO:18.

10. The nucleic acid sequence of claim 1, wherein the nucleic acid sequence comprises SEQ ID NO:33.

11. The nucleic acid sequence of claim 1, wherein the nucleic acid sequence comprises SEQ ID NO:35.

12. The nucleic acid sequence of claim 1, wherein the nucleic acid sequence comprises SEQ ID NO:36.

13. The nucleic acid sequence of claim 1, wherein the nucleic acid sequence comprises SEQ ID NO:37.

14. The nucleic acid sequence of claim 1, wherein the nucleic acid sequence comprises SEQ ID NO:39.

15. A nucleic acid sequence comprising SEQ ID NO:6.

16. A nucleic acid vector for the expression of a circovirus polypeptide comprising a heterologous promoter functionally linked to a nucleic acid encoding a polypeptide comprising an amino acid sequence selected from the group consisting of: SEQ ID NO:8, SEQ ID NO:10, SEQ ID NO:12, SEQ ID NO:14, SEQ ID NO:15, SEQ ID NO:17, SEQ ID NO:19, and SEQ ID NO:34.

17. The vector of claim 16 wherein the promoter is from a prokaryotic organism.

18. The vector of claim 16 wherein the promoter is from a eukaryotic organism.

19. A nucleic acid vector for the expression of one or more circovirus polypeptides in a eukaryotic cell comprising a eukaryotic cis-acting transcription/translation regulatory sequence functionally linked to a nucleic acid with 90% or greater homology to at least one sequence selected from the group consisting of: SEQ ID NO:3, SEQ ID NO:4, SEQ ID NO:6, SEQ ID NO:7, SEQ ID NO:9, SEQ ID NO:11, SEQ ID NO:13, SEQ ID NO:16, SEQ ID NO:18, SEQ ID NO:33, SEQ ID NO:35, SEQ ID NO:36, and SEQ ID NO:37.

20. The nucleic acid vector of claim 19 wherein the regulatory sequence is from a cytomegalovirus.

21. A nucleic acid vector for the expression of one or more circovirus polypeptides in a eukaryotic cell comprising a eukaryotic cis-acting transcription/translation regulatory sequence functionally linked to a nucleic acid sequence encoding one or more polypeptides with an amino acid sequence or sequences selected from the group consisting of: SEQ ID NO:8, SEQ ID NO:10, SEQ ID NO:12, SEQ ID NO:14, SEQ ID NO:15, SEQ ID NO:17, SEQ ID NO:19, and SEQ ID NO:34.

22. The nucleic acid vector of claim 21 wherein the regulatory sequence is from a cytomegalovirus.

* * * * *

SEQUENCE LISTING

<160> NUMBER OF SEQ ID NOS: 41

<210> SEQ ID NO 1
<211> LENGTH: 1674
<212> TYPE: DNA
<213> ORGANISM: porcine circovirus

<400> SEQUENCE: 1

```
tcagtgaaaa tgccaagcaa gaaaagcggc ccgcaacccc ataagaggtg ggtgttcacc      60
cttaataatc cttccgagga ggagaaaaac aaaatacggg agcttccaat ctcccttttt     120
gattattttg tttgcggaga ggaaggtttg gaagagggta gaactcctca cctccagggg     180
tttgcgaatt ttgctaagaa gcagactttt aacaaggtga agtggtattt tggtgcccgc     240
tgccacatcg agaaagcgaa aggaaccgac cagcagaata aagaatactg cagtaaagaa     300
ggccacatac ttatcgagtg tggagctccg cggaaccagg ggaagcgcag cgacctgtct     360
actgctgtga gtacccttt ggagacgggg tctttggtga ctgtagccga gcagttccct     420
gtaacgtatg tgagaaattt ccgcgggctg gctgaacttt tgaaagtgag cgggaagatg     480
cagcagcgtg attggaagac agctgtacac gtcatagtgg gcccgcccgg ttgtgggaag     540
agccagtggg cccgtaattt tgctgagcct agggacacct actggaagcc tagtagaaat     600
aagtggtggg atggatatca tggagaagaa gttgttgttt tggatgattt ttatggctgg     660
ttaccttggg atgatctact gagactgtgt gaccggtatc cattgactgt agagactaaa     720
gggggtactg ttcctttttt ggcccgcagt attttgatta ccagcaatca ggccccccag     780
gaatggtact cctcaactgc tgtcccagct gtagaagctc tctatcggag gattactact     840
ttgcaattt ggaagactgc tgagaacaa tccacggagg tacccgaagg ccgatttgaa     900
gcagtggacc cacctgtgc cctttccca tataaaataa attactgagt ctttttgtt     960
atcacatcgt aatggttttt atttttattt atttagaggg tcttttagga taaattctct    1020
gaattgtaca taaatagtca gccttaccac ataatttgg gctgtggctg cattttggag    1080
cgcatagccg aggcctgtgt gctcgacatt ggtgtgggta tttaaatgga gccacagctg    1140
gtttctttta ttatttgggt ggaaccaatc aattgtttgg tccagctcag gtttgggggt    1200
gaagtacctg gagtggtagg taaagggctg ccttatggtg tggcgggagg agtagttaat    1260
ataggggtca taggccaagt tggtggaggg ggttacaaag ttggcatcca agataacaac    1320
agtggaccca acacctcttt gattagaggt gatgggtct ctgggtaaa attcatattt    1380
agcctttcta atacggtagt attggaaagg tagggtagg gggttggtgc cgcctgaggg    1440
```

-continued

```
ggggaggaac tggccgatgt tgaatttgag gtagttaaca ttccaagatg gctgcgagta    1500
tcctcctttt atggtgagta caaattctgt agaaaggcgg gaattgaaga tacccgtctt    1560
tcggcgccat ctgtaacggt ttctgaaggc ggggtgtgcc aaatatggtc ttctccggag    1620
gatgtttcca agatggctgc gggggcgggt ccttcttctg cggtaacgcc tcct          1674
```

<210> SEQ ID NO 2
<211> LENGTH: 1727
<212> TYPE: DNA
<213> ORGANISM: porcine circovirus

<400> SEQUENCE: 2

```
cggcagcggc agcacctcgg cagcgtcagt gaaaatgcca agcaagaaaa gcggcccgca      60 acccataag aggtgggtgt tcaccettaa taatccttcc gaggaggaga aaaacaaaat      120
acgggagctt ccaatctccc tttttgatta ttttgtttgc ggagaggaag gtttggaaga    180
gggtagaact cctcacctcc aggggtttgc gaattttgct aagaagcaga cttttaacaa    240
ggtgaagtgg tattttggtg cccgctgcca catcgagaaa gcgaaggaa ccgaccagca    300 gaataaagaa tactgcagta aagaaggcca catacttatc gagtgtggag ctccgcggaa    360
ccaggggaag cgcagcgacc tgtctactgc tgtgagtacc cttttggaga cggggtcttt    420
ggtgactgta gccgagcagt tccctgtaac gtatgtgaga aatttccgcg ggctggctga    480
acttttgaaa gtgagcggga agatgcagca gcgtgattgg aagacagctg tacacgtcat    540
agtgggcccg cccggttgtg ggaagagcca gtgggcccgt aattttgctg agcctaggga    600
cacctactgg aagcctagta gaaataagtg gtgggatgga tatcatggag aagaagttgt    660
tgttttggat gattttatg gctggttacc ttgggatgat ctactgagac tgtgtgaccg    720
gtatccattg actgtagaga ctaaaggggg tactgttcct ttttggccc gcagtatttt    780 gattaccagc aatcaggccc cccaggaatg gtactcctca actgctgtcc cagctgtaga    840
agctctctat cggaggatta ctactttgca attttggaag actgctggag aacaatccac    900
ggaggtaccc gaaggccgat tgaagcagt ggacccaccc tgtgccctt tcccatataa    960 aataaattac tgagtctttt ttgttatcac atcgtaatgg ttttttatttt tatttatta   1020 gagggtcttt taggataaat tctctgaatt gtacataaat agtcagcctt accacataat    1080
tttgggctgt ggctgcattt tggagcgcat agccgaggcc tgtgtgctcg acattggtgt    1140
gggtatttaa atggagccac agctggtttc ttttattatt tgggtggaac caatcaattg    1200
tttggtccag ctcaggtttg gggtgaagt acctggagtg gtaggtaaag gctgccttaa    1260
tggtgtggcg ggaggagtag ttaatatagg ggtcataggc caagttggtg gagggggtta    1320
caaagttggc atccaagata acaacagtgg acccaacacc tctttgatta gaggtgatgg    1380
ggtctctggg gtaaaattca tatttagcct ttctaatacg gtagtattgg aaaggtaggg    1440 gtaggggggtt ggtgccgcct gaggggggga ggaactggcc gatgttgaat tgaggtagt    1500 taacattcca agatggctgc gagtatcctc ctttatggt gagtacaaat tctgtagaaa    1560
ggcgggaatt gaagataccc gtctttcggc gccatctgta acggtttctg aaggcgggt    1620 gtgccaaata tggtcttctc cggaggatgt ttccaagatg gctgcgggg cgggtccttc    1680 ttctgcggta acgcctcctt ggccacgtca tcctataaaa gtgaaag              1727
```

<210> SEQ ID NO 3
<211> LENGTH: 1913
<212> TYPE: DNA

-continued

<213> ORGANISM: beak and feather disease virus

<400> SEQUENCE: 3
agggaggagt aaatggcgcc gttaggcgcc cgttaatctc cggaggatca cactcgtccg 60
ggaaccatcc cgtccaagga gggctctggc tgtcgccgtt ggtgtttcac tcttaacaac 120
cctacagacg gcgaaatcga attcgtccgt tctctcgggc ctgacgaatt ctactatgcc 180
atcgttggac gggaaaaggg tgagcaaggc actccccatt tgcaaggcta ctttcatttt 240
aaaaataaga agcgactgag cgcgcttaag aaaatgctgc cgcgaggtca ttttgagcgc 300
gctaaaggga gcgacgcgga taacgagaag tattgcagta aagaggggga cgtcatactt 360
accctgggca ttgtggcgag agacggtcac cgcgctttcg atggagctgt tgctgccgtg 420
atgtccggac ccaaaatgaa ggaagtcgcg cgagagttcc cagatatcta cgtcaggcat 480
gggcggggct tgcatagcct ctcgctattg gttggttccc gcccgcgtga ttttaagact 540
gaggttgacg tcatttacgg gccaccgggg tgtggcaaga gtcgatgggc caatgagcag 600
cctgggacca aatattataa aatgcgcggt gaatggtggg atggatatga tggggaagat 660
gtcgtcatct tggacgactt ttatgggtgg ctaccttatt gcgagatgct ccgcctctgc 720
gaccgttacc cacataaagt gccagttaag ggcgcttttg tggagtttac gagcaagagg 780
atcattatca cgagcaataa ggccccggag acctggtaca aggaggactg tgacccgaag 840
ccactgttcc ggagattcac tcgtgtttgg tggtacaaca ttgacaagtt ggaacaagtc 900
cggcctgatt tcctcgccca ccccatcaat ttttgatagt ctcggtgatg tttaataaag 960
ttaggcgtcg ggccgaaggc ccgatgccgc aggggggac cccctgccgg agggttcgca 1020
gggccgtcag gcccgagaac ccgaccagcc cggagggcct agtctgtatc ggggggggg 1080 ccccgggggg tccccccgac acgacgaaca cggtagcgac gaaggcgcca ataaacactc 1140
aaaaaggtat ttgctgcttg agtctttatt aagtactggg attgttaggg gcaaactgac 1200
ggaattgaac atatatagtg agcttggtta cataagtgat cgtttgttct ggctgaggga 1260
agctgaagcc aatgccgtag tgcctgactt tcgctcctgc tgcgttgggt cctccttgta 1320
gtgggatcca gccggttctg gcgctgttta gccacaatgc tgcagactgg ttcgctgtgg 1380
tgaggtcgtt tatcgttatt tgtggttttg gtctgaggag acgtttgaat cccctgctaa 1440
cataccattt tctggcaccg tcgaaaggtg ccagtgggtc ttgtgtttgg tctgcaacag 1500
ttttaaattt acttatcctg gagtcttgga ttacggccgt gtggccgaat ccgtctcctt 1560
gtatggtgta gtgtccccat gtgggcctca tttccatttt agctaactta atccggtagt 1620
tttcgaaatt cagtgtttgt gggtttggtg tgtttgttat gaagtctgac aatgcaaagg 1680
ttacaaagtc ggagctaaaa attaggttgc cagtactggt ggtttgtttt tgaatttgga 1740
atttgaattg gcgtgtgagt ctgagagtgt aaaccctatt ggttgagaaa cggcgtctgc 1800
ggaagtgtct acgtcgccgg cggtatcgcc tgatgtgacg tctgcggtag tatgggcggg 1860
cataccgtcg tctaacctga aatatagcgc atgcgtagtt agaggtgccc cat 1913

<210> SEQ ID NO 4
<211> LENGTH: 1964
<212> TYPE: DNA
<213> ORGANISM: beak and feather disease virus

<400> SEQUENCE: 4
gggcaccggg gcaccgcagc tattggctgc cttgcggagg tgcccgcccc tagggaggag 60
taaatggcgc cgttaggcgc ccgttaatct ccggaggatc acactcgtcc gggaaccatc 120

-continued

```
ccgtccaagg agggctctgg ctgtcgccgt tggtgtttca ctcttaacaa ccctacagac      180
ggcgaaatcg aattcgtccg ttctctcggg cctgacgaat tctactatgc catcgttgga      240
cgggaaaagg gtgagcaagg cactccccat ttgcaaggct actttcattt taaaaataag      300
aagcgactga gcgcgcttaa gaaaatgctg ccgcgaggtc attttgagcg cgctaaaggg      360
agcgacgcgg ataacgagaa gtattgcagt aaagaggggg acgtcatact taccctgggc      420
attgtggcga gagacggtca ccgcgctttc gatggagctg ttgctgccgt gatgtccgga      480
cccaaaatga aggaagtcgc gcgagagttc ccagatatct acgtcaggca tgggcggggc      540
ttgcatagcc tctcgctatt ggttggttcc cgcccgcgtg attttaagac tgaggttgac      600
gtcatttacg gccaccggg gtgtggcaag agtcgatggg ccaatgagca gcctgggacc      660
aaatattata aaatgcgcgg tgaatggtgg gatggatatg atggggaaga tgtcgtcatc      720
ttggacgact tttatgggtg ctaccttat tgcgagatgc tccgcctctg cgaccgttac      780
ccacataaag tgccagttaa gggcgctttt gtggagttta cgagcaagag gatcattatc      840
acgagcaata aggccccgga gacctggtac aaggaggact gtgacccgaa gccactgttc      900
cggagattca ctcgtgtttg gtggtacaac attgacaagt tggaacaagt ccggcctgat      960
ttcctcgccc accccatcaa ttttttgatag tctcggtgat gtttaataaa gttaggcgtc     1020
gggccgaagg cccgatgccg cagggggga ccccctgccg gagggttcgc agggccgtca     1080
ggcccgagaa cccgaccagc ccggagggcc tagtctgtat cgggggggg gccccggggg     1140
gtccccccga cacgacgaac acggtagcga cgaaggcgcc aataaacact caaaaggta     1200
tttgctgctt gagtctttat taagtactgg gattgttagg ggcaaactga cggaattgaa     1260
catatatagt gagcttggtt acataagtga tcgtttgttc tggctgaggg aagctgaagc     1320
caatgccgta gtgcctgact ttcgctcctg ctgcgttggg tcctccttgt agtgggatcc     1380
agccggttct ggcgctgttt agccacaatg ctgcagactg gttcgctgtg gtgaggtcgt     1440
ttatcgttat ttgtggtttt ggtctgagga gacgtttgaa tcccctgcta acataccatt     1500
ttctggcacc gtcgaaaggt gccagtgggt cttgtgtttg gtctgcaaca gttttaaatt     1560
tacttatcct ggagtcttgg attacggccg tgtggccgaa tccgtctcct tgtatggtgt     1620
agtgtcccca tgtgggcctc atttccattt tagctaactt aatccggtag ttttcgaaat     1680
tcagtgtttg tgggtttggt gtgtttgtta tgaagtctga caatgcaaag gttacaaagt     1740
cggagctaaa aattaggttg ccagtactgg tggtttgttt ttgaatttgg aatttgaatt     1800
ggcgtgtgag tctgagagtg taaaccctat tggttgagaa acggcgtctg cggaagtgtc     1860
tacgtcgccg gcggtatcgc ctgatgtgac gtctgcggta gtatgggcgg gcataccgtc     1920
gtctaacctg aaatatagcg catgcgtagt tagaggtgcc ccat                      1964
```

<210> SEQ ID NO 5
<211> LENGTH: 32
<212> TYPE: DNA
<213> ORGANISM: porcine circovirus

<400> SEQUENCE: 5

```
aagtgcgctg ctgtagtatt accagcgcac tt                                     32
```

<210> SEQ ID NO 6
<211> LENGTH: 28
<212> TYPE: DNA
<213> ORGANISM: beak and feather disease virus -continued

<400> SEQUENCE: 6

```
aggcggcggt tagtattacc cgccgcct                                    28

<210> SEQ ID NO 7
<211> LENGTH: 660
<212> TYPE: DNA
<213> ORGANISM: beak and feather disease virus
<220> FEATURE:
<221> NAME/KEY: CDS
<222> LOCATION: (1)...(660)

<400> SEQUENCE: 7 atg ctg ccg cga ggt cat ttt gag cgc gct aaa ggg agc gac gcg gat       48
Met Leu Pro Arg Gly His Phe Glu Arg Ala Lys Gly Ser Asp Ala Asp
 1               5                  10                  15 aac gag aag tat tgc agt aaa gag ggg gac gtc ata ctt acc ctg ggc       96
Asn Glu Lys Tyr Cys Ser Lys Glu Gly Asp Val Ile Leu Thr Leu Gly
            20                  25                  30 att gtg gcg aga gac ggt cac cgc gct ttc gat gga gct gtt gct gcc      144
Ile Val Ala Arg Asp Gly His Arg Ala Phe Asp Gly Ala Val Ala Ala
        35                  40                  45 gtg atg tcc gga ccc aaa atg aag gaa gtc gcg cga gag ttc cca gat      192
Val Met Ser Gly Pro Lys Met Lys Glu Val Ala Arg Glu Phe Pro Asp
    50                  55                  60 atc tac gtc agg cat ggg cgg ggc ttg cat agc ctc tcg cta ttg gtt      240
Ile Tyr Val Arg His Gly Arg Gly Leu His Ser Leu Ser Leu Leu Val
 65                  70                  75                  80 ggt tcc cgc ccg cgt gat ttt aag act gag gtt gac gtc att tac ggg      288
Gly Ser Arg Pro Arg Asp Phe Lys Thr Glu Val Asp Val Ile Tyr Gly
                85                  90                  95 cca ccg ggg tgt ggc aag agt cga tgg gcc aat gag cag cct ggg acc      336
Pro Pro Gly Cys Gly Lys Ser Arg Trp Ala Asn Glu Gln Pro Gly Thr
            100                 105                 110 aaa tat tat aaa atg cgc ggt gaa tgg tgg gat gga tat gat ggg gaa      384
Lys Tyr Tyr Lys Met Arg Gly Glu Trp Trp Asp Gly Tyr Asp Gly Glu
        115                 120                 125 gat gtc gtc atc ttg gac gac ttt tat ggg tgg cta cct tat tgc gag      432
Asp Val Val Ile Leu Asp Asp Phe Tyr Gly Trp Leu Pro Tyr Cys Glu
    130                 135                 140 atg ctc cgc ctc tgc gac cgt tac cca cat aaa gtg cca gtt aag ggc      480
Met Leu Arg Leu Cys Asp Arg Tyr Pro His Lys Val Pro Val Lys Gly
145                 150                 155                 160 gct ttt gtg gag ttt acg agc aag agg atc att atc acg agc aat aag      528
Ala Phe Val Glu Phe Thr Ser Lys Arg Ile Ile Ile Thr Ser Asn Lys
                165                 170                 175 gcc ccg gag acc tgg tac aag gag gac tgt gac ccg aag cca ctg ttc      576
Ala Pro Glu Thr Trp Tyr Lys Glu Asp Cys Asp Pro Lys Pro Leu Phe
            180                 185                 190 cgg aga ttc act cgt gtt tgg tgg tac aac att gac aag ttg gaa caa      624
Arg Arg Phe Thr Arg Val Trp Trp Tyr Asn Ile Asp Lys Leu Glu Gln
        195                 200                 205 gtc cgg cct gat ttc ctc gcc cac ccc atc aat ttt                      660
Val Arg Pro Asp Phe Leu Ala His Pro Ile Asn Phe
    210                 215                 220

<210> SEQ ID NO 8
<211> LENGTH: 220
<212> TYPE: PRT
<213> ORGANISM: beak and feather disease virus

<400> SEQUENCE: 8
```

-continued

```
Met Leu Pro Arg Gly His Phe Glu Arg Ala Lys Gly Ser Asp Ala Asp
 1               5                  10                  15

Asn Glu Lys Tyr Cys Ser Lys Glu Gly Asp Val Ile Leu Thr Leu Gly
            20                  25                  30

Ile Val Ala Arg Asp Gly His Arg Ala Phe Asp Gly Ala Val Ala Ala
        35                  40                  45

Val Met Ser Gly Pro Lys Met Lys Glu Val Ala Arg Glu Phe Pro Asp
    50                  55                  60

Ile Tyr Val Arg His Gly Arg Gly Leu His Ser Leu Ser Leu Leu Val
65                  70                  75                  80

Gly Ser Arg Pro Arg Asp Phe Lys Thr Glu Val Asp Val Ile Tyr Gly
                85                  90                  95

Pro Pro Gly Cys Gly Lys Ser Arg Trp Ala Asn Glu Gln Pro Gly Thr
            100                 105                 110

Lys Tyr Tyr Lys Met Arg Gly Glu Trp Trp Asp Gly Tyr Asp Gly Glu
        115                 120                 125

Asp Val Val Ile Leu Asp Asp Phe Tyr Gly Trp Leu Pro Tyr Cys Glu
    130                 135                 140

Met Leu Arg Leu Cys Asp Arg Tyr Pro His Lys Val Pro Val Lys Gly
145                 150                 155                 160

Ala Phe Val Glu Phe Thr Ser Lys Arg Ile Ile Ile Thr Ser Asn Lys
                165                 170                 175

Ala Pro Glu Thr Trp Tyr Lys Glu Asp Cys Asp Pro Lys Pro Leu Phe
            180                 185                 190

Arg Arg Phe Thr Arg Val Trp Trp Tyr Asn Ile Asp Lys Leu Glu Gln
        195                 200                 205

Val Arg Pro Asp Phe Leu Ala His Pro Ile Asn Phe
    210                 215                 220

<210> SEQ ID NO 9
<211> LENGTH: 474
<212> TYPE: DNA
<213> ORGANISM: beak and feather disease virus
<220> FEATURE:
<221> NAME/KEY: CDS
<222> LOCATION: (1)...(474)

<400> SEQUENCE: 9 atg ggc ggg gct tgc ata gcc tct cgc tat tgg ttg gtt ccc gcc cgc       48
Met Gly Gly Ala Cys Ile Ala Ser Arg Tyr Trp Leu Val Pro Ala Arg
 1               5                  10                  15 gtg att tta aga ctg agg ttg acg tca ttt acg ggc cac cgg ggt gtg       96
Val Ile Leu Arg Leu Arg Leu Thr Ser Phe Thr Gly His Arg Gly Val
            20                  25                  30 gca aga gtc gat ggg cca atg agc agc ctg gga cca aat att ata aaa      144
Ala Arg Val Asp Gly Pro Met Ser Ser Leu Gly Pro Asn Ile Ile Lys
        35                  40                  45 tgc gcg gtg aat ggt ggg atg gat atg atg ggg aag atg tcg tca tct      192
Cys Ala Val Asn Gly Gly Met Asp Met Met Gly Lys Met Ser Ser Ser
    50                  55                  60 tgg acg act ttt atg ggt ggc tac ctt att gcg aga tgc tcc gcc tct      240
Trp Thr Thr Phe Met Gly Gly Tyr Leu Ile Ala Arg Cys Ser Ala Ser
65                  70                  75                  80 gcg acc gtt acc cac ata aag tgc cag tta agg gcg ctt ttg tgg agt      288
Ala Thr Val Thr His Ile Lys Cys Gln Leu Arg Ala Leu Leu Trp Ser
                85                  90                  95 tta cga gca aga gga tca tta tca cga gca ata agg ccc cgg aga cct      336
Leu Arg Ala Arg Gly Ser Leu Ser Arg Ala Ile Arg Pro Arg Arg Pro
```

```
                    100                 105                 110
ggt aca agg agg act gtg acc cga agc cac tgt tcc gga gat tca ctc      384
Gly Thr Arg Arg Thr Val Thr Arg Ser His Cys Ser Gly Asp Ser Leu
            115                 120                 125 gtg ttt ggt ggt aca aca ttg aca agt tgg aac aag tcc ggc ctg att      432
Val Phe Gly Gly Thr Thr Leu Thr Ser Trp Asn Lys Ser Gly Leu Ile
    130                 135                 140 tcc tcg ccc acc cca tca att ttt gat agt ctc ggt gat gtt              474
Ser Ser Pro Thr Pro Ser Ile Phe Asp Ser Leu Gly Asp Val
145                 150                 155

<210> SEQ ID NO 10
<211> LENGTH: 158
<212> TYPE: PRT
<213> ORGANISM: beak and feather disease virus

<400> SEQUENCE: 10

Met Gly Gly

-continued

```
caa aaa ggt att tgc tgc ttg agt ctt tat                              222
Gln Lys Gly Ile Cys Cys Leu Ser Leu Tyr
 65                  70
```

<210> SEQ ID NO 12
<211> LENGTH: 74
<212> TYPE: PRT
<213> ORGANISM: beak and feather disease virus

<400> SEQUENCE: 12

```
Met Phe Asn Lys Val Arg Arg Arg Ala Glu Gly Pro Met Pro Gln Gly
 1               5                  10                  15

Gly Thr Pro Cys Arg Arg Val Arg Arg Ala Val Arg Pro Glu Asn Pro
             20                  25                  30

Thr Ser Pro Glu Gly Leu Val Cys Ile Gly Gly Ala Pro Gly Gly
         35                  40                  45

Pro Pro Asp Thr Thr Asn Thr Val Ala Thr Lys Ala Pro Ile Asn Thr
     50                  55                  60

Gln Lys Gly Ile Cys Cys Leu Ser Leu Tyr
 65                  70
```

<210> SEQ ID NO 13
<211> LENGTH: 732
<212> TYPE: DNA
<213> ORGANISM: beak and feather disease virus
<220> FEATURE:
<221> NAME/KEY: CDS
<222> LOCATION: (1)...(732)

<400> SEQUENCE: 13

```
tct aac tac gca tgc gct ata ttt cag gtt aga cga cgg tat gcc cgc   48
Ser Asn Tyr Ala Cys Ala Ile Phe Gln Val Arg Arg Arg Tyr Ala Arg
 1               5                  10                  15 cca tac tac cgc aga cgt cac atc agg cga tac cgc gga cga cgt aga   96
Pro Tyr Tyr Arg Arg Arg His Ile Arg Arg Tyr Arg Arg Arg Arg Arg
             20                  25                  30 cac ttc cgc aga cgc cgt ttc tca acc aat agg gtt tac act ctc aga  144
His Phe Arg Arg Arg Arg Phe Ser Thr Asn Arg Val Tyr Thr Leu Arg
         35                  40                  45 ctc aca cgc caa ttc aaa ttc caa att caa aaa caa acc acc agt act  192
Leu Thr Arg Gln Phe Lys Phe Gln Ile Gln Lys Gln Thr Thr Ser Thr
     50                  55                  60 ggc aac cta att ttt agc tcc gac ttt gta acc ttt gca ttg tca gac  240
Gly Asn Leu Ile Phe Ser Ser Asp Phe Val Thr Phe Ala Leu Ser Asp
 65                  70                  75                  80 ttc ata aca aac aca cca aac cca caa aca ctg aat ttc gaa aac tac  288
Phe Ile Thr Asn Thr Pro Asn Pro Gln Thr Leu Asn Phe Glu Asn Tyr
                 85                  90                  95 cgg att aag tta gct aaa atg gaa atg agg ccc aca tgg gga cac tac  336
Arg Ile Lys Leu Ala Lys Met Glu Met Arg Pro Thr Trp Gly His Tyr
            100                 105                 110 acc ata caa gga gac gga ttc ggc cac acg gcc gta atc caa gac tcc  384
Thr Ile Gln Gly Asp Gly Phe Gly His Thr Ala Val Ile Gln Asp Ser
        115                 120                 125 agg ata agt aaa ttt aaa act gtt gca gac caa aca caa gac cca ctg  432
Arg Ile Ser Lys Phe Lys Thr Val Ala Asp Gln Thr Gln Asp Pro Leu
    130                 135                 140 gca cct ttc gac ggt gcc aga aaa tgg tat gtt agc agg gga ttc aaa  480
Ala Pro Phe Asp Gly Ala Arg Lys Trp Tyr Val Ser Arg Gly Phe Lys
145                 150                 155                 160 cgt ctc ctc aga cca aaa cca caa ata acg ata aac gac ctc acc aca  528
```

```
Arg Leu Leu Arg Pro Lys Pro Gln Ile Thr Ile Asn Asp Leu Thr Thr
                165                 170                 175 gcg aac cag tct gca gca ttg tgg cta aac agc gcc aga acc ggc tgg     576
Ala Asn Gln Ser Ala Ala Leu Trp Leu Asn Ser Ala Arg Thr Gly Trp
        180                 185                 190 atc cca cta caa gga gga ccc aac gca gca gga gcg aaa gtc agg cac     624
Ile Pro Leu Gln Gly Gly Pro Asn Ala Ala Gly Ala Lys Val Arg His
195                 200                 205 tac ggc att ggc ttc agc ttc cct cag cca gaa caa acg atc act tat     672
Tyr Gly Ile Gly Phe Ser Phe Pro Gln Pro Glu Gln Thr Ile Thr Tyr
    210                 215                 220 gta acc aag ctc act ata tat gtt caa ttc cgt cag ttt gcc cct aac     720
Val Thr Lys Leu Thr Ile Tyr Val Gln Phe Arg Gln Phe Ala Pro Asn
225                 230                 235                 240 aat ccc agt act                                                     732
Asn Pro Ser Thr <210> SEQ ID NO 14
<211> LENGTH: 244
<212> TYPE: PRT
<213> ORGANISM: beak and feather disease virus

<400> SEQUENCE: 14

Ser Asn Tyr Ala Cys Ala Ile Phe Gln Val Arg Arg Tyr Ala Arg
1               5                   10                  15

Pro Tyr Tyr Arg Arg Arg His Ile Arg Arg Tyr Arg Arg Arg Arg
            20                  25                  30

His Phe Arg Arg Arg Arg Phe Ser Thr Asn Arg Val Tyr Thr Leu Arg
            35                  40                  45

Leu Thr Arg Gln Phe Lys Phe Gln Ile Gln Lys Gln Thr Thr Ser Thr
    50                  55                  60

Gly Asn Leu Ile Phe Ser Ser Asp Phe Val Thr Phe Ala Leu Ser Asp
65                  70                  75                  80

Phe Ile Thr Asn Thr Pro Asn Pro Gln Thr Leu Asn Phe Glu Asn Tyr
                85                  90                  95

Arg Ile Lys Leu Ala Lys Met Glu Met Arg Pro Thr Trp Gly His Tyr
            100                 105                 110

Thr Ile Gln Gly Asp Gly Phe Gly His Thr Ala Val Ile Gln Asp Ser
        115                 120                 125

Arg Ile Ser Lys Phe Lys Thr Val Ala Asp Gln Thr Gln Asp Pro Leu
    130                 135                 140

Ala Pro Phe Asp Gly Ala Arg Lys Trp Tyr Val Ser Arg Gly Phe Lys
145                 150                 155                 160

Arg Leu Leu Arg Pro Lys Pro Gln Ile Thr Ile Asn Asp Leu Thr Thr
                165                 170                 175

Ala Asn Gln Ser Ala Ala Leu Trp Leu Asn Ser Ala Arg Thr Gly Trp
        180                 185                 190

Ile Pro Leu Gln Gly Gly Pro Asn Ala Ala Gly Ala Lys Val Arg His
    195                 200                 205

Tyr Gly Ile Gly Phe Ser Phe Pro Gln Pro Glu Gln Thr Ile Thr Tyr
    210                 215                 220

Val Thr Lys Leu Thr Ile Tyr Val Gln Phe Arg Gln Phe Ala Pro Asn
225                 230                 235                 240

Asn Pro Ser Thr

<210> SEQ ID NO 15
```

-continued

```
<211> LENGTH: 142
<212> TYPE: PRT
<213> ORGANISM: beak and feather disease virus

<400> SEQUENCE: 15

<210> SEQ ID NO 18
<211> LENGTH: 471
<212> TYPE: DNA
<213> ORGANISM: beak and feather disease virus
<220> FEATURE:
<221> NAME/KEY: CDS
<222> LOCATION: (1)...(471)

<400> SEQUENCE: 18 atg caa gcc ccg ccc atg cct gac gta gat atc tgg gaa ctc tcg cgc 48
Met Gln Ala Pro Pro Met Pro Asp Val Asp Ile Trp Glu Leu Ser Arg
1 5 10 15 gac ttc ctt cat ttt ggg tcc gga cat cac ggc agc aac agc tcc atc 96
Asp Phe Leu His Phe Gly Ser Gly His His Gly Ser Asn Ser Ser Ile
20 25 30 gaa agc gcg gtg acc gtc tct cgc cac aat gcc cag ggt aag tat gac 144
Glu Ser Ala Val Thr Val Ser Arg His Asn Ala Gln Gly Lys Tyr Asp
35 40 45 gtc ccc ctc ttt act gca ata ctt ctc gtt atc cgc gtc gct ccc ttt 192
Val Pro Leu Phe Thr Ala Ile Leu Leu Val Ile Arg Val Ala Pro Phe
50 55 60 agc gcg ctc aaa atg acc tcg cgg cag cat ttt ctt aag cgc gct cag 240
Ser Ala Leu Lys Met Thr Ser Arg Gln His Phe Leu Lys Arg Ala Gln
65 70 75 80 tcg ctt ctt att ttt aaa atg aaa gta gcc ttg caa atg ggg agt gcc 288
Ser Leu Leu Ile Phe Lys Met Lys Val Ala Leu Gln Met Gly Ser Ala
85 90 95 ttg ctc acc ctt ttc ccg tcc aac gat ggc ata gta gaa ttc gtc agg 336
Leu Leu Thr Leu Phe Pro Ser Asn Asp Gly Ile Val Glu Phe Val Arg
100 105 110 ccc gag aga acg gac gaa ttc gat ttc gcc gtc tgt agg gtt gtt aag 384
Pro Glu Arg Thr Asp Glu Phe Asp Phe Ala Val Cys Arg Val Val Lys
115 120 125 agt gaa aca cca acg gcg aca gcc aga gcc ctc ctt gga cgg gat ggt 432
Ser Glu Thr Pro Thr Ala Thr Ala Arg Ala Leu Leu Gly Arg Asp Gly
130 135 140 tcc cgg acg agt gtg atc ctc cgg aga tta acg ggc gcc 471
Ser Arg Thr Ser Val Ile Leu Arg Arg Leu Thr Gly Ala
145 150 155

<210> SEQ ID NO 19
<211> LENGTH: 157
<212> TYPE: PRT
<213> ORGANISM: beak and feather disease virus

<400> SEQUENCE: 19

Met Gln Ala Pro Pro Met Pro Asp Val Asp Ile Trp Glu Leu Ser Arg
1 5 10 15

Asp Phe Leu His Phe Gly Ser Gly His His Gly Ser Asn Ser Ser Ile
20 25 30

Glu Ser Ala Val Thr Val Ser Arg His Asn Ala Gln Gly Lys Tyr Asp
35 40 45

Val Pro Leu Phe Thr Ala Ile Leu Leu Val Ile Arg Val Ala Pro Phe
50 55 60

Ser Ala Leu Lys Met Thr Ser Arg Gln His Phe Leu Lys Arg Ala Gln
65 70 75 80

Ser Leu Leu Ile Phe Lys Met Lys Val Ala Leu Gln Met Gly Ser Ala
85 90 95

Leu Leu Thr Leu Phe Pro Ser Asn Asp Gly Ile Val Glu Phe Val Arg

```
                       100                 105                 110
Pro Glu Arg Thr Asp Glu Phe Asp Phe Ala Val Cys Arg Val Val Lys
            115                 120                 125

Ser Glu Thr Pro Thr Ala Thr Ala Arg Ala Leu Leu Gly Arg Asp Gly
        130                 135                 140

Ser Arg Thr Ser Val Ile Leu Arg Arg Leu Thr Gly Ala
145                 150                 155

<210> SEQ ID NO 20
<211> LENGTH: 936
<212> TYPE: DNA
<213> ORGANISM: porcine circovirus
<220> FEATURE:
<221> NAME/KEY: CDS
<222> LOCATION: (1)...(936)

<400> SEQUENCE: 20 atg cca agc aag aaa agc ggc ccg caa ccc cat aag agg tgg gtg ttc      48
Met Pro Ser Lys Lys Ser Gly Pro Gln Pro His Lys Arg Trp Val Phe
 1               5                  10                  15 acc ctt aat aat cct tcc gag gag gag aaa aac aaa ata cgg gag ctt      96
Thr Leu Asn Asn Pro Ser Glu Glu Glu Lys Asn Lys Ile Arg Glu Leu
                20                  25                  30 cca atc tcc ctt ttt gat tat ttt gtt tgc gga gag gaa ggt ttg gaa     144
Pro Ile Ser Leu Phe Asp Tyr Phe Val Cys Gly Glu Glu Gly Leu Glu
            35                  40                  45 gag ggt aga act cct cac ctc cag ggg ttt gcg aat ttt gct aag aag     192
Glu Gly Arg Thr Pro His Leu Gln Gly Phe Ala Asn Phe Ala Lys Lys
        50                  55                  60 cag act ttt aac aag gtg aag tgg tat ttt ggt gcc cgc tgc cac atc     240
Gln Thr Phe Asn Lys Val Lys Trp Tyr Phe Gly Ala Arg Cys His Ile
 65                  70                  75                  80 gag aaa gcg aaa gga acc gac cag cag aat aaa gaa tac tgc agt aaa     288
Glu Lys Ala Lys Gly Thr Asp Gln Gln Asn Lys Glu Tyr Cys Ser Lys
                85                  90                  95 gaa ggc cac ata ctt atc gag tgt gga gct ccg cgg aac cag ggg aag     336
Glu Gly His Ile Leu Ile Glu Cys Gly Ala Pro Arg Asn Gln Gly Lys
            100                 105                 110 cgc agc gac ctg tct act gct gtg agt acc ctt ttg gag acg ggg tct     384
Arg Ser Asp Leu Ser Thr Ala Val Ser Thr Leu Leu Glu Thr Gly Ser
        115                 120                 125 ttg gtg act gta gcc gag cag ttc cct gta acg tat gtg aga aat ttc     432
Leu Val Thr Val Ala Glu Gln Phe Pro Val Thr Tyr Val Arg Asn Phe
        130                 135                 140 cgc ggg ctg gct gaa ctt ttg aaa gtg agc ggg aag atg cag cag cgt     480
Arg Gly Leu Ala Glu Leu Leu Lys Val Ser Gly Lys Met Gln Gln Arg
145                 150                 155                 160 gat tgg aag aca gct gta cac gtc ata gtg ggc ccg ccc ggt tgt ggg     528
Asp Trp Lys Thr Ala Val His Val Ile Val Gly Pro Pro Gly Cys Gly
                165                 170                 175 aag agc cag tgg gcc cgt aat ttt gct gag cct agg gac acc tac tgg     576
Lys Ser Gln Trp Ala Arg Asn Phe Ala Glu Pro Arg Asp Thr Tyr Trp
            180                 185                 190 aag cct agt aga aat aag tgg tgg gat gga tat cat gga gaa gaa gtt     624
Lys Pro Ser Arg Asn Lys Trp Trp Asp Gly Tyr His Gly Glu Glu Val
        195                 200                 205 gtt gtt ttg gat gat ttt tat ggc tgg tta cct tgg gat gat cta ctg     672
Val Val Leu Asp Asp Phe Tyr Gly Trp Leu Pro Trp Asp Asp Leu Leu
    210                 215                 220 aga ctg tgt gac cgg tat cca ttg act gta gag act aaa ggg ggt act     720
```

```
Arg Leu Cys Asp Arg Tyr Pro Leu Thr Val Glu Thr Lys Gly Gly Thr
225                 230                 235                 240 gtt cct ttt ttg gcc cgc agt att ttg att acc agc aat cag gcc ccc     768
Val Pro Phe Leu Ala Arg Ser Ile Leu Ile Thr Ser Asn Gln Ala Pro
                    245                 250                 255 cag gaa tgg tac tcc tca act gct gtc cca gct gta gaa gct ctc tat     816
Gln Glu Trp Tyr Ser Ser Thr Ala Val Pro Ala Val Glu Ala Leu Tyr
                260                 265                 270 cgg agg att act act ttg caa ttt tgg aag act gct gga gaa caa tcc     864
Arg Arg Ile Thr Thr Leu Gln Phe Trp Lys Thr Ala Gly Glu Gln Ser
                275                 280                 285 acg gag gta ccc gaa ggc cga ttt gaa gca gtg gac cca ccc tgt gcc     912
Thr Glu Val Pro Glu Gly Arg Phe Glu Ala Val Asp Pro Pro Cys Ala
290                 295                 300 ctt ttc cca tat aaa ata aat tac                                     936
Leu Phe Pro Tyr Lys Ile Asn Tyr
305                 310

<210> SEQ ID NO 21
<211> LENGTH: 312
<212> TYPE: PRT
<213> ORGANISM: porcine circovirus

<400> SEQUENCE: 21

Met Pro Ser Lys Lys Ser Gly Pro Gln Pro His Lys Arg Trp Val Phe
1               5                   10                  15

Thr Leu Asn Asn Pro Ser Glu Glu Lys Asn Lys Ile Arg Glu Leu
                20                  25                  30

Pro Ile Ser Leu Phe Asp Tyr Phe Val Cys Gly Glu Glu Gly Leu Glu
                35                  40                  45

Glu Gly Arg Thr Pro His Leu Gln Gly Phe Ala Asn Phe Ala Lys Lys
            50                  55                  60

Gln Thr Phe Asn Lys Val Lys Trp Tyr Phe Gly Ala Arg Cys His Ile
65                  70                  75                  80

Glu Lys Ala Lys Gly Thr Asp Gln Gln Asn Lys Glu Tyr Cys Ser Lys
                85                  90                  95

Glu Gly His Ile Leu Ile Glu Cys Gly Ala Pro Arg Asn Gln Gly Lys
                100                 105                 110

Arg Ser Asp Leu Ser Thr Ala Val Ser Thr Leu Leu Glu Thr Gly Ser
            115                 120                 125

Leu Val Thr Val Ala Glu Gln Phe Pro Val Thr Tyr Val Arg Asn Phe
130                 135                 140

Arg Gly Leu Ala Glu Leu Leu Lys Val Ser Gly Lys Met Gln Gln Arg
145                 150                 155                 160

Asp Trp Lys Thr Ala Val His Val Ile Val Gly Pro Pro Gly Cys Gly
                165                 170                 175

Lys Ser Gln Trp Ala Arg Asn Phe Ala Glu Pro Arg Asp Thr Tyr Trp
                180                 185                 190

Lys Pro Ser Arg Asn Lys Trp Trp Asp Gly Tyr His Gly Glu Glu Val
            195                 200                 205

Val Val Leu Asp Asp Phe Tyr Gly Trp Leu Pro Trp Asp Asp Leu Leu
210                 215                 220

Arg Leu Cys Asp Arg Tyr Pro Leu Thr Val Glu Thr Lys Gly Gly Thr
225                 230                 235                 240

Val Pro Phe Leu Ala Arg Ser Ile Leu Ile Thr Ser Asn Gln Ala Pro
                245                 250                 255
```

-continued

```
Gln Glu Trp Tyr Ser Ser Thr Ala Val Pro Ala Val Glu Ala Leu Tyr
            260                 265                 270
Arg Arg Ile Thr Thr Leu Gln Phe Trp Lys Thr Ala Gly Glu Gln Ser
            275                 280                 285
Thr Glu Val Pro Glu Gly Arg Phe Glu Ala Val Asp Pro Pro Cys Ala
            290                 295                 300
Leu Phe Pro Tyr Lys Ile Asn Tyr
305                 310

<210> SEQ ID NO 22
<211> LENGTH: 285
<212> TYPE: DNA
<213> ORGANISM: porcine circovirus
<220> FEATURE:
<221> NAME/KEY: CDS
<222> LOCATION: (1)...(285)

<400> SEQUENCE: 22 atg gag cca cag ctg gtt tct ttt att att tgg gtg gaa cca atc aat      48
Met Glu Pro Gln Leu Val Ser Phe Ile Ile Trp Val Glu Pro Ile Asn
 1               5                  10                  15 tgt ttg gtc cag ctc agg ttt ggg ggt gaa gta cct gga gtg gta ggt      96
Cys Leu Val Gln Leu Arg Phe Gly Gly Glu Val Pro Gly Val Val Gly
            20                  25                  30 aaa ggg ctg cct tat ggt gtg gcg gga gga gta gtt aat ata ggg gtc     144
Lys Gly Leu Pro Tyr Gly Val Ala Gly Gly Val Val Asn Ile Gly Val
        35                  40                  45 ata ggc caa gtt ggt gga ggg ggt tac aaa gtt ggc atc caa gat aac     192
Ile Gly Gln Val Gly Gly Gly Gly Tyr Lys Val Gly Ile Gln Asp Asn
    50                  55                  60 aac agt gga ccc aac acc tct ttg att aga ggt gat ggg gtc tct ggg     240
Asn Ser Gly Pro Asn Thr Ser Leu Ile Arg Gly Asp Gly Val Ser Gly
65                  70                  75                  80 gta aaa ttc ata ttt agc ctt tct aat acg gta gta ttg gaa agg         285
Val Lys Phe Ile Phe Ser Leu Ser Asn Thr Val Val Leu Glu Arg
                85                  90                  95

<210> SEQ ID NO 23
<211> LENGTH: 95
<212> TYPE: PRT
<213> ORGANISM: porcine circovirus

<400> SEQUENCE: 23

Met Glu Pro Gln Leu Val Ser Phe Ile Ile Trp Val Glu Pro Ile Asn
 1               5                  10                  15

Cys Leu Val Gln Leu Arg Phe Gly Gly Glu Val Pro Gly Val Val Gly
            20                  25                  30

Lys Gly Leu Pro Tyr Gly Val Ala Gly Gly Val Val Asn Ile Gly Val
        35                  40                  45

Ile Gly Gln Val Gly Gly Gly Gly Tyr Lys Val Gly Ile Gln Asp Asn
    50                  55                  60

Asn Ser Gly Pro Asn Thr Ser Leu Ile Arg Gly Asp Gly Val Ser Gly
65                  70                  75                  80

Val Lys Phe Ile Phe Ser Leu Ser Asn Thr Val Val Leu Glu Arg
                85                  90                  95

<210> SEQ ID NO 24
<211> LENGTH: 699
<212> TYPE: DNA
<213> ORGANISM: porcine circovirus
```

-continued

```
<400> SEQUENCE: 24
atgacgtggc caaggaggcg ttaccgcaga agaaggaccc gcccccgcag ccatcttgga        60
aacatcctcc ggagaagacc atatttggca caccccgcct tcagaaaccg ttacagatgg       120
cgccgaaaga cgggtatctt caattcccgc ctttctacag aatttgtact caccataaaa       180
ggaggatact cgcagccatc ttggaatgtt aactacctca aattcaacat cggccagttc       240
ctcccccct caggcggcac caaccccta cccctacctt tccaatacta ccgtattaga        300
aaggctaaat atgaatttta ccccagagac cccatcacct ctaatcaaag aggtgttggg       360
tccactgttg ttatcttgga tgccaacttt gtaaccccct ccaccaactt ggcctatgac       420
ccctatatta actactcctc ccgccacacc ataaggcagc cctttaccta ccactccagg       480
tacttcaccc ccaaacctga gctggaccaa acaattgatt ggttccaccc aaataataaa       540
agaaaccagc tgtggctcca tttaaatacc cacaccaatg tcgagcacac aggcctcggc       600
tatgcgctcc aaaatgcagc cacagcccaa aattatgtgg taaggctgac tatttatgta       660
caattcagag aatttatcct aaaagaccct ctaaataaa                              699

<210> SEQ ID NO 25
<211> LENGTH: 687
<212> TYPE: DNA
<213> ORGANISM: porcine circovirus
<220> FEATURE:
<221> NAME/KEY: CDS
<222> LOCATION: (1)...(687)

<400> SEQUENCE: 25 atg acg tgg cca agg agg cgt tac cgc aga aga agg acc cgc ccc cgc        48
Met Thr Trp Pro Arg Arg Arg Tyr Arg Arg Arg Thr Arg Pro Arg
 1               5                  10                  15 agc cat ctt gga aac atc ctc cgg aga aga cca tat ttg gca cac ccc        96
Ser His Leu Gly Asn Ile Leu Arg Arg Arg Pro Tyr Leu Ala His Pro
             20                  25                  30 gcc ttc aga aac cgt tac aga tgg cgc cga aag acg ggt atc ttc aat       144
Ala Phe Arg Asn Arg Tyr Arg Trp Arg Arg Lys Thr Gly Ile Phe Asn
         35                  40                  45 tcc cgc ctt tct aca gaa ttt gta ctc acc ata aaa gga gga tac tcg       192
Ser Arg Leu Ser Thr Glu Phe Val Leu Thr Ile Lys Gly Gly Tyr Ser
     50                  55                  60 cag cca tct tgg aat gtt aac tac ctc aaa ttc aac atc ggc cag ttc       240
Gln Pro Ser Trp Asn Val Asn Tyr Leu Lys Phe Asn Ile Gly Gln Phe
 65                  70                  75                  80 ctc ccc ccc tca ggc ggc acc aac ccc cta ccc cta cct ttc caa tac       288
Leu Pro Pro Ser Gly Gly Thr Asn Pro Leu Pro Leu Pro Phe Gln Tyr
                 85                  90                  95 tac cgt att aga aag gct aaa tat gaa ttt tac ccc aga gac ccc atc       336
Tyr Arg Ile Arg Lys Ala Lys Tyr Glu Phe Tyr Pro Arg Asp Pro Ile
            100                 105                 110 acc tct aat caa aga ggt gtt ggg tcc act gtt gtt atc ttg gat gcc       384
Thr Ser Asn Gln Arg Gly Val Gly Ser Thr Val Val Ile Leu Asp Ala
        115                 120                 125 aac ttt gta acc ccc tcc acc aac ttg gcc tat gac ccc tat att aac       432
Asn Phe Val Thr Pro Ser Thr Asn Leu Ala Tyr Asp Pro Tyr Ile Asn
    130                 135                 140 tac tcc tcc cgc cac acc ata agg cag ccc ttt acc tac cac tcc agg       480
Tyr Ser Ser Arg His Thr Ile Arg Gln Pro Phe Thr Tyr His Ser Arg
145                 150                 155                 160 tac ttc acc ccc aaa cct gag ctg gac caa aca att gat tgg ttc cac       528
Tyr Phe Thr Pro Lys Pro Glu Leu Asp Gln Thr Ile Asp Trp Phe His
```

```
cca aat aat aaa aga aac cag ctg tgg ctc cat tta aat acc cac acc    576
Pro Asn Asn Lys Arg Asn Gln Leu Trp Leu His Leu Asn Thr His Thr
            180                 185                 190 aat gtc gag cac aca ggc ctc ggc tat gcg ctc caa aat gca gcc aca    624
Asn Val Glu His Thr Gly Leu Gly Tyr Ala Leu Gln Asn Ala Ala Thr
        195                 200                 205 gcc caa aat tat gtg gta agg ctg act att tat gta caa ttc aga gaa    672
Ala Gln Asn Tyr Val Val Arg Leu Thr Ile Tyr Val Gln Phe Arg Glu
    210                 215                 220 ttt atc cta aaa gac                                                687
Phe Ile Leu Lys Asp
225
```

<210> SEQ ID NO 26
<211> LENGTH: 229
<212> TYPE: PRT
<213> ORGANISM: porcine circovirus

<400> SEQUENCE: 26

```
Met Thr Trp Pro Arg Arg Arg Tyr Arg Arg Arg Thr Arg Pro Arg
1               5                   10                  15

Ser His Leu Gly Asn Ile Leu Arg Arg Arg Pro Tyr Leu Ala His Pro
            20                  25                  30

Ala Phe Arg Asn Arg Tyr Arg Trp Arg Arg Lys Thr Gly Ile Phe Asn
        35                  40                  45

Ser Arg Leu Ser Thr Glu Phe Val Leu Thr Ile Lys Gly Gly Tyr Ser
    50                  55                  60

Gln Pro Ser Trp Asn Val Asn Tyr Leu Lys Phe Asn Ile Gly Gln Phe
65                  70                  75                  80

Leu Pro Pro Ser Gly Gly Thr Asn Pro Leu Pro Leu Pro Phe Gln Tyr
                85                  90                  95

Tyr Arg Ile Arg Lys Ala Lys Tyr Glu Phe Tyr Pro Arg Asp Pro Ile
            100                 105                 110

Thr Ser Asn Gln Arg Gly Val Gly Ser Thr Val Val Ile Leu Asp Ala
        115                 120                 125

Asn Phe Val Thr Pro Ser Thr Asn Leu Ala Tyr Asp Pro Tyr Ile Asn
    130                 135                 140

Tyr Ser Ser Arg His Thr Ile Arg Gln Pro Phe Thr Tyr His Ser Arg
145                 150                 155                 160

Tyr Phe Thr Pro Lys Pro Glu Leu Asp Gln Thr Ile Asp Trp Phe His
                165                 170                 175

Pro Asn Asn Lys Arg Asn Gln Leu Trp Leu His Leu Asn Thr His Thr
            180                 185                 190

Asn Val Glu His Thr Gly Leu Gly Tyr Ala Leu Gln Asn Ala Ala Thr
        195                 200                 205

Ala Gln Asn Tyr Val Val Arg Leu Thr Ile Tyr Val Gln Phe Arg Glu
    210                 215                 220

Phe Ile Leu Lys Asp
225
```

<210> SEQ ID NO 27
<211> LENGTH: 618
<212> TYPE: DNA
<213> ORGANISM: porcine circovirus
<220> FEATURE:
<221> NAME/KEY: CDS
<222> LOCATION: (1)...(618)

<400> SEQUENCE: 27

```
atg ata tcc atc cca cca ctt att tct act agg ctt cca gta ggt gtc      48
Met Ile Ser Ile Pro Pro Leu Ile Ser Thr Arg Leu Pro Val Gly Val
 1               5                  10                  15 cct agg ctc agc aaa att acg ggc cca ctg gct ctt ccc aca acc ggg      96
Pro Arg Leu Ser Lys Ile Thr Gly Pro Leu Ala Leu Pro Thr Thr Gly
             20                  25                  30 cgg gcc cac tat gac gtg tac agc tgt ctt cca atc acg ctg ctg cat     144
Arg Ala His Tyr Asp Val Tyr Ser Cys Leu Pro Ile Thr Leu Leu His
         35                  40                  45 ctt ccc gct cac ttt caa aag ttc agc cag ccc gcg gaa att tct cac     192
Leu Pro Ala His Phe Gln Lys Phe Ser Gln Pro Ala Glu Ile Ser His
     50                  55                  60 ata cgt tac agg gaa ctg ctc ggc tac agt cac caa aga ccc cgt ctc     240
Ile Arg Tyr Arg Glu Leu Leu Gly Tyr Ser His Gln Arg Pro Arg Leu
 65                  70                  75                  80 caa aag ggt act cac agc agt aga cag gtc gct gcg ctt ccc ctg gtt     288
Gln Lys Gly Thr His Ser Ser Arg Gln Val Ala Ala Leu Pro Leu Val
                 85                  90                  95 ccg cgg agc tcc aca ctc gat aag tat gtg gcc ttc ttt act gca gta     336
Pro Arg Ser Ser Thr Leu Asp Lys Tyr Val Ala Phe Phe Thr Ala Val
            100                 105                 110 ttc ttt att ctg ctg gtc ggt tcc ttt cgc ttt ctc gat gtg gca gcg     384
Phe Phe Ile Leu Leu Val Gly Ser Phe Arg Phe Leu Asp Val Ala Ala
        115                 120                 125 ggc acc aaa ata cca ctt cac ctt gtt aaa agt ctg ctt ctt agc aaa     432
Gly Thr Lys Ile Pro Leu His Leu Val Lys Ser Leu Leu Leu Ser Lys
    130                 135                 140 att cgc aaa ccc ctg gag gtg agg agt tct acc ctc ttc caa acc ttc     480
Ile Arg Lys Pro Leu Glu Val Arg Ser Ser Thr Leu Phe Gln Thr Phe
145                 150                 155                 160 ctc tcc gca aac aaa ata atc aaa aag gga gat tgg aag ctc ccg tat     528
Leu Ser Ala Asn Lys Ile Ile Lys Lys Gly Asp Trp Lys Leu Pro Tyr
                165                 170                 175 ttt gtt ttt ctc ctc ctc gga agg att att aag ggt gaa cac cca cct     576
Phe Val Phe Leu Leu Leu Gly Arg Ile Ile Lys Gly Glu His Pro Pro
            180                 185                 190 ctt atg ggg ttg cgg gcc gct ttt ctt gct tgg cat ttt cac             618
Leu Met Gly Leu Arg Ala Ala Phe Leu Ala Trp His Phe His
        195                 200                 205

<210> SEQ ID NO 28
<211> LENGTH: 206
<212> TYPE: PRT
<213> ORGANISM: porcine circovirus

<400> SEQUENCE: 28

Met Ile Ser Ile Pro Pro Leu Ile Ser Thr Arg Leu Pro Val Gly Val
 1               5                  10                  15

Pro Arg Leu Ser Lys Ile Thr Gly Pro Leu Ala Leu Pro Thr Thr Gly
             20                  25                  30

Arg Ala His Tyr Asp Val Tyr Ser Cys Leu Pro Ile Thr Leu Leu His
         35                  40                  45

Leu Pro Ala His Phe Gln Lys Phe Ser Gln Pro Ala Glu Ile Ser His
     50                  55                  60

Ile Arg Tyr Arg Glu Leu Leu Gly Tyr Ser His Gln Arg Pro Arg Leu
 65                  70                  75                  80

Gln Lys Gly Thr His Ser Ser Arg Gln Val Ala Ala Leu Pro Leu Val
```

```
                    85                   90                    95
Pro Arg Ser Ser Thr Leu Asp Lys Tyr Val Ala Phe Phe Thr Ala Val
                100                 105                 110

Phe Phe Ile Leu Leu Val Gly Ser Phe Arg Phe Leu Asp Val Ala Ala
            115                 120                 125

Gly Thr Lys Ile Pro Leu His Leu Val Lys Ser Leu Leu Leu Ser Lys
        130                 135                 140

Ile Arg Lys Pro Leu Glu Val Arg Ser Ser Thr Leu Phe Gln Thr Phe
145                 150                 155                 160

Leu Ser Ala Asn Lys Ile Ile Lys Lys Gly Asp Trp Lys Leu Pro Tyr
                165                 170                 175

Phe Val Phe Leu Leu Gly Arg Ile Ile Lys Gly Glu His Pro Pro
            180                 185                 190

Leu Met Gly Leu Arg Ala Ala Phe Leu Ala Trp His Phe His
        195                 200                 205

<210> SEQ ID NO 29
<211> LENGTH: 609
<212> TYPE: DNA
<213> ORGANISM: porcine circovirus
<220> FEATURE:
<221> NAME/KEY: CDS
<222> LOCATION: (1)...(609)

<400> SEQUENCE: 29 atg ata tcc atc cca cca ctt att tct act agg ctt cca gta ggt gtc        48
Met Ile Ser Ile Pro Pro Leu Ile Ser Thr Arg Leu Pro Val Gly Val
  1               5                  10                  15 cct agg ctc agc aaa att acg ggc cca ctg gct ctt ccc aca acc ggg        96
Pro Arg Leu Ser Lys Ile Thr Gly Pro Leu Ala Leu Pro Thr Thr Gly
                 20                  25                  30 cgg gcc cac tat gac gtg tac agc tgt ctt cca atc acg ctg ctg cat       144
Arg Ala His Tyr Asp Val Tyr Ser Cys Leu Pro Ile Thr Leu Leu His
             35                  40                  45 ctt ccc gct cac ttt caa aag ttc agc cag ccc gcg gaa att tct cac       192
Leu Pro Ala His Phe Gln Lys Phe Ser Gln Pro Ala Glu Ile Ser His
         50                  55                  60 ata cgt tac agg gaa ctg ctc ggc tac agt cac caa aga ccc cgt ctc       240
Ile Arg Tyr Arg Glu Leu Leu Gly Tyr Ser His Gln Arg Pro Arg Leu
 65                  70                  75                  80 caa aag ggt act cac agc agt aga cag gtc gct gcg ctt ccc ctg gtt       288
Gln Lys Gly Thr His Ser Ser Arg Gln Val Ala Ala Leu Pro Leu Val
                 85                  90                  95 ccg cgg agc tcc aca ctc gat aag tat gtg gcc ttc ttt act gca gta       336
Pro Arg Ser Ser Thr Leu Asp Lys Tyr Val Ala Phe Phe Thr Ala Val
                100                 105                 110 ttc ttt att ctg ctg gtc ggt tcc ttt cgc ttt ctc gat gtg gca gcg       384
Phe Phe Ile Leu Leu Val Gly Ser Phe Arg Phe Leu Asp Val Ala Ala
            115                 120                 125 ggc acc aaa ata cca ctt cac ctt gtt aaa agt ctg ctt ctt agc aaa       432
Gly Thr Lys Ile Pro Leu His Leu Val Lys Ser Leu Leu Leu Ser Lys
        130                 135                 140 att cgc aaa ccc ctg gag gtg agg agt tct acc ctc ttc caa acc ttc       480
Ile Arg Lys Pro Leu Glu Val Arg Ser Ser Thr Leu Phe Gln Thr Phe
145                 150                 155                 160 ctc tcc gca aac aaa ata atc aaa aag gga gat tgg aag ctc ccg tat       528
Leu Ser Ala Asn Lys Ile Ile Lys Lys Gly Asp Trp Lys Leu Pro Tyr
                165                 170                 175 ttt gtt ttt ctc ctc ctc gga agg att att aag ggt gaa cac cca cct       576
```

```
Phe Val Phe Leu Leu Leu Gly Arg Ile Ile Lys Gly Glu His Pro Pro
            180                 185                 190 ctt atg ggg ttg cgg gcc gct ttt ctt gct tgg                              609
Leu Met Gly Leu Arg Ala Ala Phe Leu Ala Trp
        195                 200

<210> SEQ ID NO 30
<211> LENGTH: 203
<212> TYPE: PRT
<213> ORGANISM: porcine circovirus

<400> SEQUENCE: 30

Met Ile Ser Ile Pro Pro Leu Ile Ser Thr Arg Leu Pro Val Gly Val
 1               5                  10                  15

Pro Arg Leu Ser Lys Ile Thr Gly Pro Leu Ala Leu Pro Thr Thr Gly
            20                  25                  30

Arg Ala His Tyr Asp Val Tyr Ser Cys Leu Pro Ile Thr Leu Leu His
        35                  40                  45

Leu Pro Ala His Phe Gln Lys Phe Ser Gln Pro Ala Glu Ile Ser His
    50                  55                  60

Ile Arg Tyr Arg Glu Leu Leu Gly Tyr Ser His Gln Arg Pro Arg Leu
65                  70                  75                  80

Gln Lys Gly Thr His Ser Ser Arg Gln Val Ala Ala Leu Pro Leu Val
                85                  90                  95

Pro Arg Ser Ser Thr Leu Asp Lys Tyr Val Ala Phe Phe Thr Ala Val
            100                 105                 110

Phe Phe Ile Leu Leu Val Gly Ser Phe Arg Phe Leu Asp Val Ala Ala
        115                 120                 125

Gly Thr Lys Ile Pro Leu His Leu Val Lys Ser Leu Leu Ser Lys
    130                 135                 140

Ile Arg Lys Pro Leu Glu Val Arg Ser Ser Thr Leu Phe Gln Thr Phe
145                 150                 155                 160

Leu Ser Ala Asn Lys Ile Ile Lys Lys Gly Asp Trp Lys Leu Pro Tyr
                165                 170                 175

Phe Val Phe Leu Leu Leu Gly Arg Ile Ile Lys Gly Glu His Pro Pro
            180                 185                 190

Leu Met Gly Leu Arg Ala Ala Phe Leu Ala Trp
        195                 200

<210> SEQ ID NO 31
<211> LENGTH: 345
<212> TYPE: DNA
<213> ORGANISM: porcine circovirus
<220> FEATURE:
<221> NAME/KEY: CDS
<222> LOCATION: (1)...(345)

<400> SEQUENCE: 31 atg acg tgt aca gct gtc ttc caa tca cgc tgc tgc atc ttc ccg ctc       48
Met Thr Cys Thr Ala Val Phe Gln Ser Arg Cys Cys Ile Phe Pro Leu
 1               5                  10                  15 act ttc aaa agt tca gcc agc ccg cgg aaa ttt ctc aca tac gtt aca       96
Thr Phe Lys Ser Ser Ala Ser Pro Arg Lys Phe Leu Thr Tyr Val Thr
            20                  25                  30 ggg aac tgc tcg gct aca gtc acc aaa gac ccc gtc tcc aaa agg gta      144
Gly Asn Cys Ser Ala Thr Val Thr Lys Asp Pro Val Ser Lys Arg Val
        35                  40                  45 ctc aca gca gta gac agg tcg ctg cgc ttc ccc tgg ttc cgc gga gct      192
Leu Thr Ala Val Asp Arg Ser Leu Arg Phe Pro Trp Phe Arg Gly Ala
```

```
                      50                    55                    60
cca cac tcg ata agt atg tgg cct tct tta ctg cag tat tct tta ttc        240
Pro His Ser Ile Ser Met Trp Pro Ser Leu Leu Gln Tyr Ser Leu Phe
 65                  70                    75                    80 tgc tgg tcg gtt cct ttc gct ttc tcg atg tgg cag cgg gca cca aaa        288
Cys Trp Ser Val Pro Phe Ala Phe Ser Met Trp Gln Arg Ala Pro Lys
                     85                    90                    95 tac cac ttc acc ttg tta aaa gtc tgc tta gca aaa ttc gca aac            336
Tyr His Phe Thr Leu Leu Lys Val Cys Leu Ala Lys Phe Ala Asn
                 100                   105                   110 ccc tgg agg                                                             345
Pro Trp Arg
        115

<210> SEQ ID NO 32
<211> LENGTH: 115
<212> TYPE: PRT
<213> ORGANISM: porcine circovirus

<400> SEQUENCE: 32

Met Thr Cys Thr Ala Val Phe Gln Ser Arg Cys Cys Ile Phe Pro Leu
 1               5                  10                  15

Thr Phe Lys Ser Ser Ala Ser Pro Arg Lys Phe Leu Thr Tyr Val Thr
             20                  25                  30

Gly Asn Cys Ser Ala Thr Val Thr Lys Asp Pro Val Ser Lys Arg Val
         35                  40                  45

Leu Thr Ala Val Asp Arg Ser Leu Arg Phe Pro Trp Phe Arg Gly Ala
     50                  55                  60

Pro His Ser Ile Ser Met Trp Pro Ser Leu Leu Gln Tyr Ser Leu Phe
 65                  70                  75                  80

Cys Trp Ser Val Pro Phe Ala Phe Ser Met Trp Gln Arg Ala Pro Lys
                 85                  90                  95

Tyr His Phe Thr Leu Leu Lys Val Cys Leu Ala Lys Phe Ala Asn
             100                 105                 110

Pro Trp Arg
        115

<210> SEQ ID NO 33
<211> LENGTH: 207
<212> TYPE: DNA
<213> ORGANISM: beak and feather disease virus
<220> FEATURE:
<221> NAME/KEY: CDS
<222> LOCATION: (1)...(207)

<400> SEQUENCE: 33 ggg gca cct cta act acg cat gcg cta tat ttc agg tta gac gac ggt         48
Gly Ala Pro Leu Thr Thr His Ala Leu Tyr Phe Arg Leu Asp Asp Gly
 1               5                  10                  15 atg ccc gcc cat act acc gca gac gtc aca tca ggc gat acc gcc ggc         96
Met Pro Ala His Thr Thr Ala Asp Val Thr Ser Gly Asp Thr Ala Gly
             20                  25                  30 gac gta gac act tcc gca gac gcc gtt tct caa cca ata ggg ttt aca        144
Asp Val Asp Thr Ser Ala Asp Ala Val Ser Gln Pro Ile Gly Phe Thr
         35                  40                  45 ctc tca gac tca cac gcc aat tca aat tcc aaa ttc aaa aac aaa cca        192
Leu Ser Asp Ser His Ala Asn Ser Asn Ser Lys Phe Lys Asn Lys Pro
     50                  55                  60 cca gta ctg gca acc                                                    207
Pro Val Leu Ala Thr
```

-continued

<210> SEQ ID NO 34
<211> LENGTH: 69
<212> TYPE: PRT
<213> ORGANISM: beak and feather disease virus

<400> SEQUENCE: 34

Gly Ala Pro Leu Thr Thr His Ala Leu Tyr Phe Arg Leu Asp Asp Gly
 1               5                   10                  15

Met Pro Ala His Thr Thr Ala Asp Val Thr Ser Gly Asp Thr Ala Gly
            20                  25                  30

Asp Val Asp Thr Ser Ala Asp Ala Val Ser Gln Pro Ile Gly Phe Thr
        35                  40                  45

Leu Ser Asp Ser His Ala Asn Ser Asn Ser Lys Phe Lys Asn Lys Pro
    50                  55                  60

Pro Val Leu Ala Thr
65

<210> SEQ ID NO 35
<211> LENGTH: 272
<212> TYPE: DNA
<213> ORGANISM: beak and feather disease virus

<400> SEQUENCE: 35
actgcttaag atgatacggt agcaacctgc cctttccca ctcgttccgt gagggtaaa      60 cgttccgatg aaagtaaaat ttttattctt cgctgactcg cgcgaattct tttacgacgg   120
cgctccagta aaactcgcgc gatttccctc gctgcgccta ttgctcttca taacgtcatt   180
tctccccctg cagtatgaat gggacccgta acaccgctct ctgccagtgg cgcgaaagct   240
acctcgacaa cgacggcaac tacagcagcc tg                                 272

<210> SEQ ID NO 36
<211> LENGTH: 268
<212> TYPE: DNA
<213> ORGANISM: beak and feather disease virus

<400> SEQUENCE: 36
actgctaaga tatacggtag caacctgccc ttttcccgca cgttccatgg ggggtaaacg    60
ttccgatgaa agtaaaattt ttattcttcg ctgactcgcg cgaattcttt tacgacggcg   120
ctcgggtaaa actcgcgcga tttccctcgc tacgcctatt actcttcata acgtcatttc   180
tccccctgca ctatgaatgg gacccgtaac accgctctct gccagtggcg cgaaagctgc   240
ctcgacaacg acggcaacta cacagcct                                      268

<210> SEQ ID NO 37
<211> LENGTH: 267
<212> TYPE: DNA
<213> ORGANISM: beak and feather disease virus

<400> SEQUENCE: 37
actgctaaga tatacggtag gcaacctgct cttttcccgc tcgttccatg ggggtaaac     60 gttccgatga agtaaaatt tttattcttc gctgactcgc gcgaattctt ttacgacggc   120
gctcgggtaa aactcgcgcg atttccctcg ctacgcctat tactctttat aacgtcattt   180
cacccccagc actatgaatg ggacccgtaa caccgctctc tgccagtggc gcgaaagctg   240
cctcgacaac gacggcaact acacagc                                       267

-continued

<210> SEQ ID NO 38
<211> LENGTH: 1759
<212> TYPE: DNA
<213> ORGANISM: porcine circovirus

<400> SEQUENCE: 38

```
accagcgcac ttcggcagcg gcagcacctc ggcagcgtca gtgaaaatgc caagcaagaa     60
aagcggcccg caaccccata agaggtgggt gttcaccctt aataatcctt ccgaggagga    120
gaaaaacaaa atacgggagc ttccaatctc cctttttgat tattttgttt gcggagagga    180
aggtttggaa gagggtagaa ctcctcacct ccaggggttt gcgaattttg ctaagaagca    240
gacttttaac aaggtgaagt ggtattttgg tgcccgctgc cacatcgaga aagcgaaagg    300
aaccgaccag cagaataaag aatactgcag taaagaaggc cacatactta tcgagtgtgg    360
agctccgcgg aaccagggga agcgcagcga cctgtctact gctgtgagta ccctttttgga    420
gacggggtct ttggtgactg tagccgagca gttccctgta acgtatgtga gaaatttccg    480
cgggctggct gaacttttga aagtgagcgg gaagatgcag cagcgtgatt ggaagacagc    540
tgtacacgtc atagtgggcc cgcccggttg tgggaagagc cagtgggccc gtaattttgc    600
tgagcctagg gacacctact ggaagcctag tagaaataag tggtgggatg gatatcatgg    660
agaagaagtt gttgttttgg atgattttta tggctggtta ccttgggatg atctactgag    720
actgtgtgac cggtatccat tgactgtaga gactaaaggg ggtactgttc ctttttttggc    780
ccgcagtatt ttgattacca gcaatcaggc cccccaggaa tggtactcct caactgctgt    840
cccagctgta gaagctctct atcggaggat tactactttg caattttgga agactgctgg    900
agaacaatcc acggaggtac ccgaaggccg atttgaagca gtggacccac cctgtgccct    960
tttcccatat aaaataaatt actgagtctt ttttgttatc acatcgtaat ggtttttatt   1020
tttatttatt tagagggtct tttaggataa attctctgaa ttgtacataa atagtcagcc   1080
ttaccacata attttgggct gtggctgcat tttggagcgc atagccgagg cctgtgtgct   1140
cgacattggt gtgggtattt aaatggagcc acagctggtt tcttttatta tttgggtgga   1200
accaatcaat tgtttggtcc agctcaggtt tgggggtgaa gtacctggag tggtaggtaa   1260
agggctgcct tatggtgtgg cgggaggagt agttaatata ggggtcatag gccaagttgg   1320
tggagggggt tacaaagttg gcatccaaga taacaacagt ggacccaaca cctctttgat   1380
tagaggtgat ggggtctctg ggtaaaattc catatttagc ctttctaata cggtagtatt   1440
ggaaaggtag ggtagggggg ttggtgccgc ctgagggggg gaggaactgg ccgatgttga   1500
atttgaggta gttaacattc caagatggct gcgagtatcc tccttttatg gtgagtacaa   1560
attctgtaga aaggcgggaa ttgaagatac ccgtctttcg gcgccatctg taacggtttc   1620
tgaaggcggg gtgtgccaaa tatggtcttc tccggaggat gtttccaaga tggctgcggg   1680
ggcgggtcct tcttctgcgg taacgcctcc ttggccacgt catcctataa aagtgaaaga   1740
agtgcgctgc tgtagtatt                                                1759
```

<210> SEQ ID NO 39
<211> LENGTH: 1993
<212> TYPE: DNA
<213> ORGANISM: beak and feather disease virus

<400> SEQUENCE: 39

```
ttagtattac ccgccgcctg gggcaccggg gcaccgcagc tattggctgc cttgcggagg     60
tgcccgcccc tagggaggag taaatggcgc cgttaggcgc ccgttaatct ccggaggatc    120
```

```
acactcgtcc gggaaccatc ccgtccaagg agggctctgg ctgtcgccgt tggtgtttca      180
ctcttaacaa ccctacagac ggcgaaatcg aattcgtccg ttctctcggg cctgacgaat      240
tctactatgc catcgttgga cgggaaaagg gtgagcaagg cactccccat ttgcaaggct      300
actttcattt taaaaataag aagcgactga gcgcgcttaa gaaaatgctg ccgcgaggtc      360
attttgagcg cgctaaaggg agcgacgcgg ataacgagaa gtattgcagt aaagagggg      420 acgtcatact tacccctgggc attgtggcga gagacggtca ccgcgctttc gatggagctg      480
ttgctgccgt gatgtccgga cccaaaatga aggaagtcgc gcgagagttc ccagatatct      540
acgtcaggca tgggcgggc ttgcatagcc tctcgctatt ggttggttcc cgcccgcgtg      600
attttaagac tgaggttgac gtcatttacg gccaccggg gtgtggcaag agtcgatggg      660
ccaatgagca gcctgggacc aaatattata aaatgcgcgg tgaatggtgg gatggatatg      720
atggggaaga tgtcgtcatc ttggacgact tttatgggtg gctaccttat tgcgagatgc      780
tccgcctctg cgaccgttac ccacataaag tgccagttaa gggcgctttt gtggagttta      840
cgagcaagag gatcattatc acgagcaata aggccccgga gacctggtac aaggaggact      900
gtgacccgaa gccactgttc cggagattca ctcgtgtttg gtggtacaac attgacaagt      960
tggaacaagt ccggcctgat ttcctcgccc accccatcaa tttttgatag tctcggtgat     1020
gtttaataaa gttaggcgtc gggccgaagg cccgatgccg caggggggga cccctgccg     1080 gagggttcgc agggccgtca ggcccgagaa cccgaccagc ccggagggcc tagtctgtat     1140 cgggggggg gccccggggg gtccccccga cacgacgaac acggtagcga cgaaggcgcc     1200
aataaacact caaaaaggta tttgctgctt gagtctttat taagtactgg gattgttagg     1260
ggcaaactga cggaattgaa catatatagt gagcttggtt acataagtga tcgtttgttc     1320 tggctgaggaa agctgaagc caatgccgta gtgcctgact ttcgctcctg ctgcgttggg     1380
tcctccttgt agtgggatcc agccggttct ggcgctgttt agccacaatg ctgcagactg     1440
gttcgctgtg gtgaggtcgt ttatcgttat ttgtggtttt ggtctgagga acgtttgaa     1500 tccctgcta acataccatt ttctggcacc gtcgaaaggt gccagtgggt cttgtgtttg     1560
gtctgcaaca gttttaaatt tactatcct ggagtcttgg attacggccg tgtggccgaa     1620
tccgtctcct tgtatggtgt agtgtcccca tgtgggcctc atttccattt tagctaactt     1680
aatccggtag ttttcgaaat tcagtgtttg tgggtttggt gtgtttgtta tgaagtctga     1740
caatgcaaag gttacaaagt cggagctaaa aattaggttg ccagtactgg tggtttgttt     1800
ttgaatttgg aatttgaatt ggcgtgtgag tctgagagtg taaaccctat tggttgagaa     1860
acggcgtctg cggaagtgtc tacgtcgccg gcggtatcgc ctgatgtgac gtctgcggta     1920
gtatgggcgg gcataccgtc gtctaacctg aaatatagcg catgcgtagt tagaggtgcc     1980
ccataggcgg cgg                                                         1993
```

<210> SEQ ID NO 40
<211> LENGTH: 1759
<212> TYPE: DNA
<213> ORGANISM: porcine circovirus

<400> SEQUENCE: 40

```
aatactacag cagcgcactt ctttcacttt tataggatga cgtggccaag gaggcgttac       60
cgcagaagaa ggaccgccc ccgcagccat cttggaaaca tcctccggag aagaccatat      120
ttggcacacc ccgccttcag aaaccgttac agatggcgcc gaaagacggg tatcttcaat      180
```

```
tcccgccttt ctacagaatt tgtactcacc ataaaaggag gatactcgca gccatcttgg      240
aatgttaact acctcaaatt caacatcggc cagttcctcc cccctcagg cggcaccaac      300 cccctacccc tacctttcca atactaccgt attagaaagg ctaaatatga attttacccc     360
agagacccca tcacctctaa tcaaagaggt gttgggtcca ctgttgttat cttggatgcc     420
aactttgtaa cccctccac caacttggcc tatgacccct atattaacta ctcctcccgc      480
cacaccataa ggcagccctt tacctaccac tccaggtact tcaccccaa acctgagctg      540 gaccaaacaa ttgattggtt ccacccaaat aataaaagaa accagctgtg gctccattta     600
aatacccaca ccaatgtcga gcacacaggc ctcggctatg cgctccaaaa tgcagccaca     660
gcccaaaatt atgtggtaag gctgactatt tatgtacaat tcagagaatt tatcctaaaa     720
gaccctctaa ataaataaaa ataaaaacca ttacgatgtg ataacaaaaa agactcagta     780
atttatttta tatgggaaaa gggcacaggg tgggtccact gcttcaaatc ggccttcggg     840
tacctccgtg gattgttctc cagcagtctt ccaaaattgc aaagtagtaa tcctccgata     900
gagagcttct acagctggga cagcagttga ggagtaccat tcctgggggg cctgattgct     960
ggtaatcaaa atactgcggg ccaaaaaagg aacagtaccc cctttagtct ctacagtcaa    1020
tggataccgg tcacacagtc tcagtagatc atcccaaggt aaccagccat aaaaatcatc    1080
caaaacaaca acttcttctc catgatatcc atcccaccac ttatttctac taggcttcca    1140
gtaggtgtcc ctaggctcag caaaattacg ggcccactgg ctcttcccac aaccgggcgg    1200
gcccactatg acgtgtacag ctgtcttcca atcacgctgc tgcatcttcc cgtcactttt    1260
caaaagttca gccagcccgc ggaaatttct cacatacgtt acagggaact gctcggctac    1320
agtcaccaaa gaccccgtct ccaaaagggt actcacagca gtagacaggt cgctgcgctt    1380
cccctggttc cgcggagctc cacactcgat aagtatgtgg ccttctttac tgcagtattc    1440
tttattctgc tggtcggttc ctttcgcttt ctcgatgtgg cagcgggcac caaaatacca    1500
cttcaccttg ttaaaagtct gcttcttagc aaaattcgca aaccctggga ggtgaggagt    1560
tctaccctct tccaaaccctt cctctccgca aacaaaataa tcaaaagggg agattggaag   1620
ctcccgtatt ttgtttttct cctcctcgga aggattatta agggtgaaca cccacctctt    1680
atggggttgc gggccgcttt tcttgcttgg catttcact gacgctgccg aggtgctgcc     1740
gctgccgaag tgcgctggt                                                 1759

<210> SEQ ID NO 41
<211> LENGTH: 1993
<212> TYPE: DNA
<213> ORGANISM: beak and feather disease virus

<400> SEQUENCE: 41
ccgccgccta tggggcacct ctaactacgc atgcgctata tttcaggtta gacgacggta      60
tgcccgccca tactaccgca gacgtcacat caggcgatac cgccggcgac gtagacactt     120
ccgcagacgc cgtttctcaa ccaatagggt ttacactctc agactcacac gccaattcaa     180
attccaaatt caaaaacaaa ccaccagtac tggcaaccta atttttagct ccgactttgt     240 aaccttttgca ttgtcagact tcataacaaa cacaccaaac ccacaaacac tgaatttcga     300
aaactaccgg attaagttag ctaaaatgga aatgaggccc acatgggac actacaccat      360 acaaggagac ggattcggcc acacggccgt aatccaagac tccaggataa gtaaatttaa     420
aactgttgca gaccaaacac aagacccact ggcacctttc gacggtgcca gaaaatggta     480
tgttagcagg ggattcaaac gtctcctcag accaaaacca caaataacga taaacgacct     540
```

```
caccacagcg aaccagtctg cagcattgtg gctaaacagc gccagaaccg gctggatccc      600
actacaagga ggacccaacg cagcaggagc gaaagtcagg cactacggca ttggcttcag      660
cttccctcag ccagaacaaa cgatcactta tgtaaccaag ctcactatat atgttcaatt      720
ccgtcagttt gcccctaaca atcccagtac ttaataaaga ctcaagcagc aaataccttt      780
ttgagtgttt attggcgcct tcgtcgctac cgtgttcgtc gtgtcggggg gaccccccgg      840 ggccccccc  ccgatacaga ctaggccctc cgggctggtc gggttctcgg gcctgacggc      900
cctgcgaacc ctccggcagg gggtccccc  ctgcggcatc gggccttcgg cccgacgcct      960
aactttatta aacatcaccg agactatcaa aaattgatgg ggtgggcgag gaaatcaggc     1020
cggacttgtt ccaacttgtc aatgttgtac caccaaacac gagtgaatct ccggaacagt     1080
ggcttcgggt cacagtcctc cttgtaccag gtctccgggg ccttattgct cgtgataatg     1140
atcctcttgc tcgtaaactc cacaaaagcg cccttaactg gcactttatg tgggtaacgg     1200
tcgcagaggc ggagcatctc gcaataaggt agccacccat aaaagtcgtc caagatgacg     1260
acatcttccc catcatatcc atcccaccat tcaccgcgca ttttataata tttggtccca     1320
ggctgctcat tggcccatcg actcttgcca caccccggtg gcccgtaaat gacgtcaacc     1380
tcagtcttaa aatcacgcgg gcgggaacca accaatagcg agaggctatg caagcccgc     1440 ccatgcctga cgtagatatc tgggaactct cgcgcgactt ccttcatttt gggtccggac     1500
atcacggcag caacagctcc atcgaaagcg cggtgaccgt ctctcgccac aatgcccagg     1560
gtaagtatga cgtcccctc  tttactgcaa tacttctcgt tatccgcgtc gctcccttta     1620
gcgcgctcaa aatgacctcg cggcagcatt ttcttaagcg cgctcagtcg cttcttattt     1680
ttaaaatgaa agtagccttg caaatgggga gtgccttgct caccctttc  ccgtccaacg     1740 atggcatagt agaattcgtc aggcccgaga gaacggacga attcgatttc gccgtctgta     1800
gggttgttaa gagtgaaaca ccaacggcga cagccagagc cctccttgga cgggatggtt     1860
cccggacgag tgtgatcctc cggagattaa cgggcgccta acggcgccat ttactcctcc     1920 ctagggcgg  gcacctccgc aaggcagcca atagctgcgg tgccccggtg ccccaggcgg     1980
cgggtaatac taa                                                        1993
```